US009155789B2

(12) United States Patent
Tsuji

(10) Patent No.: US 9,155,789 B2
(45) Date of Patent: Oct. 13, 2015

(54) USE OF ALLOGENIC OR SYNGENIC MAJOR HISTOCOMPATIBILITY COMPLEX (MHC) MOLECULES AS UNIVERSAL ADJUVANTS FOR VACCINES AGAINST NEOPLASTIC DISEASE, INFECTION AND AUTOIMMUNE DISEASE

(75) Inventor: Moriya Tsuji, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 1302 days.

(21) Appl. No.: 11/412,149

(22) Filed: Apr. 25, 2006

(65) Prior Publication Data

US 2006/0240033 A1    Oct. 26, 2006

Related U.S. Application Data

(60) Provisional application No. 60/675,039, filed on Apr. 25, 2005.

(51) Int. Cl.
*A61K 39/00* (2006.01)
*A61K 39/39* (2006.01)
*C07K 14/74* (2006.01)

(52) U.S. Cl.
CPC ............... *A61K 39/39* (2013.01); *A61K 39/00* (2013.01); *A61K 2039/5156* (2013.01); *A61K 2039/53* (2013.01); *A61K 2039/54* (2013.01); *A61K 2039/55516* (2013.01); *A61K 2039/605* (2013.01); *A61K 2039/6006* (2013.01)

(58) Field of Classification Search
None
See application file for complete search history.

(56) References Cited

U.S. PATENT DOCUMENTS

| 5,843,435 | A | 12/1998 | Slavin |
| 6,136,306 | A | 10/2000 | Granger |
| 6,207,147 | B1 | 3/2001 | Hiserodt et al. |
| 2003/0101465 | A1* | 5/2003 | Lawman et al. ............ 800/8 |

OTHER PUBLICATIONS

Carey et al (Clinical Immunology Jul. 2005, 116: 65-76).*
Blanco et al (Current Opin. Rheumatol. 2005, 17: 731-734).*
Felix et al (J. Immunol. 2006, 176: 1062-1071).*
Nebel et al (PNAS USA 1996, 93: 15388-15393).*
Ribas et al (J. Clin. Oncol. 2003, 21(12): 2415-2432).*
Ilan et al (J. Clin. Invest. 1996, 98 (11): 2640-2647).*
Galanis (Curr. Opin. Molec. Ther. 2002, 4(1): 80-87).*
Marsh et al (The HLA Facts Book, Academic Press, San Diego, 2000, pp. 147, 152 and 104).*
Tusji (Exp. Parasitology, 2010, 126: 421-425).*
Fahey et al (Clinical Experimental Immunology, 1992, 88: 1-5).*
Letvin (Science, 1998, 280: 1875-1880).*
Machuca et al. (Intervirology 1999,42: 37-42 ).*
Caulfield MJ, Wang S, Smith JG, Tobery TW, Liu X, Davies ME, Casimiro DR, Fu TM, Simon A, Evans RK, Emini EA, Shiver J. 2002. Sustained peptide-specific gamma interferon T-cell response in rhesus macaques immunized with human immunodeficiency virus gag DNA vaccines. *J. Virol.* 76:10038-10043.
Ishimoto T, Yamamoto K, Fukui Y, Fukuda Y, Dohi K, Sasazuki T. 1997. In vitro and in vivo evidence for high frequency of I-Ab-reactive CD4+ T cells in HLA-DQ or HLA-DRA transgenic mice lacking endogenous MHC class I and/or class II expression. *J. Immunol.* 159:3717-3722.
Kobayashi E, Kawai K, Ikarashi Y, Fujiwara M. 1992. Mechanism of the rejection of major histocompatibility complex class I-disparate murine skin grafts: rejection can be mediated by CD4+ cells activated by allo-class I + II antigen in CD8+ cell-depleted hosts. *J. Exp. Med.* 176:617-621.
Lauwerys BR, Garot N, Renauld JC, Houssiau FA. 2000. Cytokine production and killer activity of NK/T-NK cells derived with IL-2, IL-15, or the combination of IL-12 and IL-18. *J. Immunol.* 165:1847-1853.
Li S, Rodrigues M, Rodriguez D, Rodriguez JR, Esteban M, Palese P, Nussenzweig RS, Zavala F. 1993. Priming with recombinant influenza virus followed by administration of recombinant vaccinia virus induces CD8+ T-cell-mediated protective immunity against malaria. *Proc. Natl. Acad. Sci. USA.* 90:5214-5218.
Martin PJ. 1990. The role of donor lymphoid cells in allogeneic marrow engraftment. *Bone Marrow Transplant.* 6:283-289.
Pasquini S, Xiang Z, Wang Y, He Z, Deng H, Blaszczyk-Thurin M, Ertl HC. 1997. Cytokines and costimulatory molecules as genetic adjuvants. *Immunol. Cell Biol.* 75:397-401.
Ramachandra L, Chu RS, Askew D, Noss EH, Canaday DH, Potter NS, Johnsen A, Krieg, AM, Nedrud JG, Boom WH, Harding CV. 1999. Phagocytic antigen processing and effects of microbial products on antigen processing and T-cell responses. *ImmunoL Rev.* 168:217-239.
Rodrigues EG, Zavala F, Eichinger D, Wilson JM, Tsuji M. 1997. Single immunizing dose of recombinant adenovirus efficiently induces CD8+ T cell-mediated protective immunity against malaria. *J. Immunol.* 158:1268-1274.
Singh M, O'Hagan D. 1999. Advances in vaccine adjuvants. *Nat. Biotechnol.* 17:1075-1081.
Suzuki T, Fukuhara T, Tanaka M, Nakamura A, Akiyama K, Sakakibara T, Koinuma D, Kikuchi T, Tazawa R, Maemondo, Hagiwara K, Saijo Y, and Nukiwa T, 2005. Vaccination of Dendritic Cells Loaded with interleukin-12-secreting cancer cells augments in vivo Antitumor Immunity: Characteristics of Syngeneic and Allogeneic Antigen-Presenting Cell Cancer Hybrid Cells. Clin. Cancer Res. 11:58-66.
Tanaka Y, Koido S, Chen D, Gendler SJ, Kufe D, Gong J. 2001. Vaccination with allogeneic dendritic cells fused to carcinoma cells induces antitumor immunity in MUC1 transgenic mice. *Clin. Immunol.* 101:192-200.

(Continued)

*Primary Examiner* — Michael Szperka
*Assistant Examiner* — Marianne Dibrino
(74) *Attorney, Agent, or Firm* — Troutman Sanders LLP

(57) ABSTRACT

The present invention is directed to the discovery that allogenic or syngenic adjuvant stimulation can cause local inflammation which increases the antigen presentation capability of cells in the vicinity of adjuvant stimulation. By discovering this phenomenon, the present invention provides a novel method for augmenting the immunogencity of an antigen by conjointly administering an allogenic or syngenic MHC molecule (as a universal adjuvant) to trigger a local inflammatory reaction to enhance antigen presentation at the site of delivery.

25 Claims, 7 Drawing Sheets

(56) References Cited

OTHER PUBLICATIONS

Figure 1:
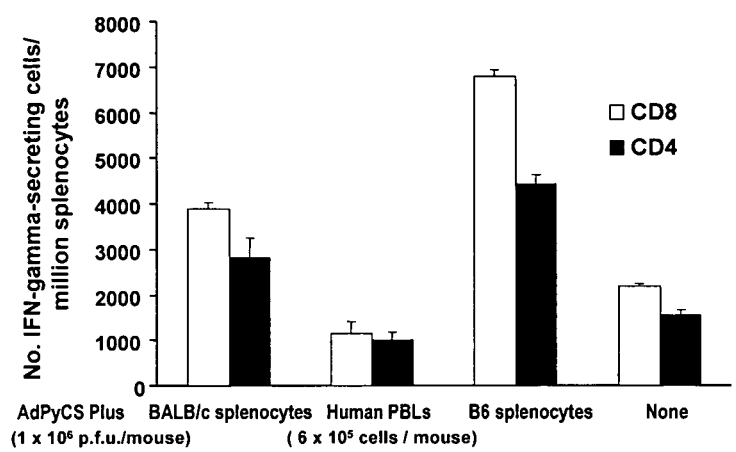

Tsuji M, Bergmann CC, Takita-Sonoda Y, Murata K, Rodrigues EG, Nussenzweig, RS, Zavala F. 1998. Recombinant Sindbis viruses expressing a cytotoxic T-lymphocyte epitope of a malaria parasite or of influenza virus elicit protection against the corresponding pathogen in mice. *J. Virol.* 72:6907-6910.

Wang Y, Tao L, Mitchell E, Bravery C, Berlingieri P, Armstrong P, Vaughan R, Underwood J, Lehner T. 1999. Allo-immunization elicits CD8+ T cell-derived chemokines, HIV suppressor factors and resistance to HIV infection in women. *Nat. Med.* 5:1004-1009.

Warren TL, Weiner GJ. 2000. Uses of granulocyte-macrophage colony-stimulating factor in vaccine development. *Curr. Opin. Hematol.* 7:168-173.

Zhai Y, Hong X, Wang J, Fechner JH, Goodman RE, Johnson MC, Knechtle SJ. 1998. Modulation of alloimmunity to major histocompatibility complex class I by cotransfer of cytokine genes in vivo. *Transpl. Immunol.* 6:169-75.

Linda A. Sherman and Suchismita Chattopadhyay. The Molecular Basis of Allorecognition ; *Annu. Rev. Immunol*, 1993, 11:385-402.

W.L. Ford and R.C. Atkins. The Proportion of Lympocyters Capable of Recognizing Strong Transplantation Antigens in Vivo. *Adv. Exp. Med. Biol.* 1973,29:255-262.

W.L. Ford, S.J. Simmonds and R.C. Atkins. Early Cellular Events in a Systemic Graft-vs-Host Reaction; *The Journal of Experimental Medicine*, vol. 141, pp. 681-696 1975.

Amara et al., Different patterns of immune responses but similar control of a simian-human immunodeficiency virus 89.6P mucosal challenge by modified vaccinia virus Ankara (MVA) and DNA/MVA vaccines., *Journal of Virology*, vol. 76,No. 15: Aug. 2002, p. 7625-7631.

Elliott et al., Cytotoxic T. lymphocytes recognize a reconstituted class I histocompatibility antigen (HLA-A2) as an allogeneic target molecule, *Proc. Natl. Acad. Sci. USA*, vol. 87: Jul. 1990, p. 5213-5217.

Fried et al., Recombinant dimeric MHC antigens protect cardiac allografts from rejection and visualize alloreactive T cells, *J. Leukocyte Biology*, vol. 78: Sep. 2005, p. 595-604.

Hafalla et al., Short-term antigen presentation and single clonal burst limit the magnitude of the CD8+ T cell responses to malaria liver stages, *PNAS*, vol. 99 No. 18: Sep. 2002, p. 11819-11824, & 14611.

Hess et al., Modulation of Graft-versus-Host Disease: Role of Regulatory T Lymphocytes, *BB&MT*: (2006), p. 13-21.

Mempel et al., T-Cell priming by dendritic cells in lymph nodes occurs in three distinct phases, *Nature*, vol. 427: Jan. 2004, p. 154-159.

Obst et al., The Role of Peptides in T Cell Alloreactivity Is Determined by Self-Major Histocompatibility Complex Molecules, *J. Exp. Med.*, vol. 191, No. 5: Mar. 2000, p. 805-812.

Rickert et al., A Divalent Human Leukocyte Antigen-B7 Fusion-Protein Up-regulates CD25 and CD69 in Alloreactive CD8 + T Cells Bypassing CD28 Costimulation, *Transplantation*, vol. 81, No. 9: May 2006, p. 1337-1344.

Smith et al., Peptide-independent Recognition by Alloreactive Cytotoxic T Lymphocytes (CTL), Journal Exp. Med., vol. 185, No. 6: Mar. 1997, p. 1023-1033.

Epstein, et al. "Live Attenuated Malaria Vaccine Designed to Protect Through Hepatic CD8+ T Cell Immunity" Science 2011, 334:475-480.

Horowitz, et al. "Use of Immobilized HLA-A2:Ig Dimeric Proteins to Determine the Level of Epitope-Specific, HLA-Restricted CD8+ T-Cell Response" Scandinavian Journal of Immunology 2009, 70:415-422.

Seder, et al. "Protection Against Malaria by Intravenous Immunization with a Nonreplicating Sporozoite Vaccine" Science 2013, 341:1359-1365.

Stevanovic, et al. "Human allo-reactive CD4+ T cells as strong mediators of anti-tumor immunity in NOD/scid mice engrafted with human acute lymphoblastic leukemia" Leukemia 2012, 26:312-322.

Teirlinck, et al. "Longevity and Composition of Cellular Immune Responses Following Experimental *Plasmodium falciparum* Malaria Infection in Humans" PLos Pathogens 2011, 7(12):e1002389.

\* cited by examiner

Schematic map of pVAX1

Schematic map of pADVAX

Schematic map of ADVAX1

Gag-specific CD8+ T cell response after co-administration of DNA-Gag Vaccine and DNA encoding H-2K$^b$ gene

```
                         SEQUENCE LISTING

<160> NUMBER OF SEQ ID NOS: 25

<210> SEQ ID NO 1
<211> LENGTH: 21
<212> TYPE: PRT
<213> ORGANISM: Malaria

<400> SEQUENCE: 1

Tyr Asn Arg Asn Ile Val Asn Arg Leu Leu Gly Asp Ala Leu Asn Gly
1               5                   10                  15

Lys Pro Glu Glu Lys
            20

<210> SEQ ID NO 2
<211> LENGTH: 9
<212> TYPE: PRT
<213> ORGANISM: Malaria

<400> SEQUENCE: 2

Ser Tyr Val Pro Ser Ala Glu Gln Ile
1               5

<210> SEQ ID NO 3
<211> LENGTH: 8
<212> TYPE: PRT
<213> ORGANISM: Malaria

<400> SEQUENCE: 3

Asn Val Asp Pro Asn Ala Asn Pro
1               5

<210> SEQ ID NO 4
<211> LENGTH: 20
<212> TYPE: PRT
<213> ORGANISM: Malaria

<400> SEQUENCE: 4

Glu Tyr Leu Asn Lys Ile Gln Asn Ser Leu Ser Thr Glu Trp Ser Pro
1               5                   10                  15

Cys Ser Val Thr
            20

<210> SEQ ID NO 5
<211> LENGTH: 10
<212> TYPE: PRT
<213> ORGANISM: Human immunodeficiency virus

<400> SEQUENCE: 5

Arg Gly Pro Gly Arg Ala Phe Val Thr Ile
1               5                   10

<210> SEQ ID NO 6
<211> LENGTH: 11
<212> TYPE: PRT
<213> ORGANISM: Human immunodeficiency virus

<400> SEQUENCE: 6

Lys Ala Phe Ser Pro Glu Val Ile Pro Met Phe
```

<210> SEQ ID NO 7
<211> LENGTH: 8
<212> TYPE: PRT
<213> ORGANISM: Human immunodeficiency virus

<400> SEQUENCE: 7

Lys Ala Phe Ser Pro Glu Val Ile
1               5

<210> SEQ ID NO 8
<211> LENGTH: 9
<212> TYPE: PRT
<213> ORGANISM: Human immunodeficiency virus

<400> SEQUENCE: 8

Thr Pro Gln Asp Leu Asn Met Met Leu
1               5

<210> SEQ ID NO 9
<211> LENGTH: 9
<212> TYPE: PRT
<213> ORGANISM: Human immunodeficiency virus

<400> SEQUENCE: 9

Thr Pro Gln Asp Leu Asn Thr Met Leu
1               5

<210> SEQ ID NO 10
<211> LENGTH: 10
<212> TYPE: PRT
<213> ORGANISM: Human immunodeficiency virus

<400> SEQUENCE: 10

Asp Thr Ile Asn Glu Glu Ala Ala Glu Trp
1               5                   10

<210> SEQ ID NO 11
<211> LENGTH: 10
<212> TYPE: PRT
<213> ORGANISM: Human immunodeficiency virus

<400> SEQUENCE: 11

Lys Arg Trp Ile Ile Leu Gly Leu Asn Lys
1               5                   10

<210> SEQ ID NO 12
<211> LENGTH: 9
<212> TYPE: PRT
<213> ORGANISM: Human immunodeficiency virus

<400> SEQUENCE: 12

Gln Ala Thr Gln Glu Val Lys Asn Trp
1               5

<210> SEQ ID NO 13
<211> LENGTH: 9
<212> TYPE: PRT
<213> ORGANISM: Human immunodeficiency virus

<400> SEQUENCE: 13

Arg Leu Arg Pro Gly Gly Lys Lys Lys
1               5

```
<210> SEQ ID NO 14
<211> LENGTH: 9
<212> TYPE: PRT
<213> ORGANISM: Human immunodeficiency virus

<400> SEQUENCE: 14

Ser Leu Tyr Asn Thr Val Ala Thr Leu
1               5

<210> SEQ ID NO 15
<211> LENGTH: 9
<212> TYPE: PRT
<213> ORGANISM: Homo sapiens

<400> SEQUENCE: 15

Leu Pro Tyr Leu Gly Trp Leu Val Phe
1               5

<210> SEQ ID NO 16
<211> LENGTH: 45
<212> TYPE: PRT
<213> ORGANISM: artificial
<220> FEATURE:
<223> OTHER INFORMATION: synthetic peptide

<400> SEQUENCE: 16

Met Leu Pro Tyr Leu Gly Trp Leu Val Phe Ala Gln His Pro Asn Ala
1               5                   10                  15

Glu Leu Leu Lys His Tyr Leu Phe Arg Asn Leu Ser Pro Ser Tyr Val
            20                  25                  30

Tyr His Gln Phe Ile Pro Asn Pro Leu Leu Gly Leu Asp
        35                  40                  45

<210> SEQ ID NO 17
<211> LENGTH: 23
<212> TYPE: PRT
<213> ORGANISM: Artificial
<220> FEATURE:
<223> OTHER INFORMATION: Leader Sequence

<400> SEQUENCE: 17

Met Asp Ala Met Lys Arg Gly Leu Cys Cys Val Leu Leu Leu Cys Gly
1               5                   10                  15

Ala Val Phe Val Ser Ala Arg
            20

<210> SEQ ID NO 18
<211> LENGTH: 2520
<212> TYPE: DNA
<213> ORGANISM: Artificial
<220> FEATURE:
<223> OTHER INFORMATION: TPA-ENV-optimized sequence

<400> SEQUENCE: 18
atggatgcaa tgaagagggg gctctgctgt gtgctgctgc tgtgtggagc agtcttcgtt     60
agcgccgccg agaacttgtg ggtgaccgtg tactacggcg tgcccgtgtg gaaggaggcc    120
aagaccaccc tgttctgcgc ctccgacgcc aaggcctacg agaaggaggt gcacaacgtg    180
tgggccaccc acgcctgcgt gcccaccgac cccaaccccc aggagatggt gttggagaac    240
gtgaccgaga acttcaacat gtggaagaac gacatggtga accagatgca cgaggacgtc    300
atcagcttgt gggaccagag cctgaagccc tgcgtgaagt tgacccccct gtgcgtgacc    360
```

```
ttggagtgca ggaacgtgag cagcaacggc acctacaacg agacctacaa cgagatcaag    420
aactgctcct tcaacgccac caccgtgttg agggacagga agcagaccgt gtacgccctg    480
ttctacaggc tggacatcgt gcccctgaac aagaagaact ccagcgagaa ctccagcgag    540
tactacaggt tgatcaactg caacacctcc gccatcaccc aggcctgccc caaggtgacc    600
ttcgacccca tccccatcca ctactgcacc cccgccggct acgccatcct gaagtgcaac    660
gacaagacct tcaacggcac cggccccgtgc acaacgtga gcaccgtgca gtgcacccac    720
ggcatcaagc ccgtggtgtc cacccagctg ctgttgaacg gcagcctggc cgagagggag    780
atcatcatca ggtccgagaa cctgaccaac aacgtgaaga ccatcatcgt gcacctgaac    840
cagtccgtgg agatcgtgtg caccaggccc aacaacaaca ccaggaagag catcaggatc    900
ggccccggcc agaccttcta cgccaccggc gacatcatcg gcgacatcag gcaggcccac    960
tgcaacatca gcaaggacaa gtggaaggag accttgcaga gggtgggcaa gaagttggcc   1020
gagcacttcc ccaacaagac catcgagttc gcctcctcct ccggcggcga cctggagatc   1080
accacccaca gcttcaactg caggggcgag ttcttctact gcaacacctc cagcctgttc   1140
aacggcacct acatgcccaa cggcaccgag ggcaactcca gctccatcat caccatcccc   1200
tgcaggatca agcagatcat caacatgtgg caggaggtgg gccgcgccat gtacgccccc   1260
cccatcgagg gcaacatcac ctgcaagtcc aacatcaccg gcctgctgtt ggtgcgcgac   1320
ggcggcaagg agaccaacga caccgagacc ttcaggcccg gcggcggcga catgagggac   1380
aactggagga gcgagttgta caagtacaag gtggtggaga tcaagcccct tgggcatcgcc   1440 cccaccgccg ccaagaggag ggtggtggag agggagaaga gggccgtggg catcggcgcc   1500
gtgttcctgg gcttcctggg cgccgccggc agcaccatgg gcgccgccag catcaccctg   1560
accgtgcagg cccgccagct gctgagcggc atcgtgcagc agcagagcaa cctgctgcgc   1620
gccatcgagg cccagcagca cctgctgcag ctgaccgtgt ggggcatcaa gcagctgcag   1680
acccgcgttc tggccatcga gcgctacctg aaggaccagc agctgctggg catctggggc   1740
tgcagcggca gctgatctg caccaccgcc gtgcactgga acagcagctg gagcaaccgc   1800
agccaggagg agatctggaa caacatgacc tggatgcagt gggaccgcga gatcagcaac   1860
tacaccaaca ccatctaccg cctgctggag gacagccaga accagcagga gcgcaacgag   1920
aaggacctgc tggccctgga caactggaag aacctgtgga gctggttcga catcaccaac   1980
tggctgtggt acatccgcat cttcatcatg atcgtgggcg gcctgatcgg cctgcgcatc   2040
atcttcgccg tgctgagcat cgtgaaccgc gtgcgccagg gctacagccc cctgagcttc   2100 cagacccctga ccccccaaccc cggcggcccc gaccgcctgg gccgcatcga ggaggagggc   2160
ggcgagcagg acaagaaccg cagcatccgc ctggtgaacg gcttcctggc cctggcctgg   2220
gacgacctgc gcaacctgtg ccgcttcagc taccacctgc tgcgcgacct gctgctgatc   2280
gtggcccgca tcgtggagct gctgggccgc cgcggctggg aggccctgcg ctactggtgg   2340
aacctgctga agactgggt gcaggagctg aagaacagcg ccgtgagcct gctgaacgcc   2400
accgccatcg ccgtggccga gggcaccgac cgcgtgatcg aggtggtgca gggcgcctac   2460
cgcgccatcc tgcacatccc ccgccgcatc cgccagggct cgaggccgc cctgcagtaa   2520
```

<210> SEQ ID NO 19
<211> LENGTH: 1545
<212> TYPE: DNA
<213> ORGANISM: Artificial
<220> FEATURE:
<223> OTHER INFORMATION: TPA-GAG-optimized-sequence -continued

<400> SEQUENCE: 19

```
atggacgcca tgaagcgcgg cctgtgctgc gtgctgctgc tgtgcggcgc cgtgttcgtg      60
agcgcccgca tgggcgcccg cgccagcatc ctgcgcggcg gcaagctggg caagtgggag     120
aagatccgcc tgcgccccgg cgacaagaag cactacatgc tgaagcacct ggtgtgggcc     180
agccgcgagc tggagcgctt cgccctgaac cccggcctgc tggagaccag cgagggctgc     240
aagcagatca tcaagcagct gcagcccgcc ctgcagaccg gcaccgagga gctgcgcagc     300
ctgttcaaca ccgtggccac cctgtactgc gtgcacgagg gcatcgagat ccgcgacacc     360
aaggaggccc tggacaagat cgaggaggag cagaacaaga tccagcagaa gacccagcag     420
gccaagaagg ccgacgagaa ggtgagccag aactacccca tcgtgcagaa cctgcagggc     480
cagatggtgc accaggccat ctcccccagg accttgaacg cctgggtgaa ggtgatcgag     540
gagaaggcct tcagccccga ggtgatcccc atgttcaccg ccttgtccga gggcgccacc     600
cccaggact  tgaacaccat gttgaacacc gtgggcggcc accaggccgc catgcagatg     660
ttgaaggaca ccatcaacga ggaggccgcc gagtgggaca gggtgcaccc cgtgcacgcc     720
ggccccattg cccccggcca gatgagggag cccaggggca cgacatcgc cggcaccacc     780
agcaccctgc agggccagat cgcctggatg accagcaacc ccccgtgcc cgtgggcgag     840
atctacaaga ggtggatcat cctgggcttg aacaagatcg tgaggatgta cagccccgtg     900
agcatcttgg acatcaagca gggccccaag gagcccttca gggactacgt ggaccgcttc     960
ttcaagacct tgagggccga gcaggccacc caggacgtga agaactggat gaccgacacc    1020
tgttggtgc  agaacgccaa ccccgactgc aagaccatct tgagggcctt gggccccggc    1080
gcctccttgg aggagatgat gaccgcctgc caggggcgtgg gcggcccag  ccacaaggcc   1140
agggtgttgg ccgaggccat gagccaggcc aacggcacca tcctgatgca gaggagcaac    1200
ttcaagggct ccaagaggat cgtgaagtgc ttcaactgcg gcaaggaggg ccacatcgcc    1260
aggaactgca gggcccccag gaagaagggc tgctggaagt gcggcaagga gggccaccag    1320
atgaaggact gcaccgagag caggccaac  ttcttgggca agatctggcc ctcccacaag    1380
ggcaggcccg gcaacttcct gcagagcagg cccgagccca ccgccccccc cgccgagagc    1440
ttcaggttcg aggagaccac ccccgccccc aagcaggagc caaggacag  ggagccctg     1500
acctccctga gtccctgtt  cggcagcgac cccttgtccc agtaa                    1545
```

<210> SEQ ID NO 20
<211> LENGTH: 491
<212> TYPE: PRT
<213> ORGANISM: Human immunodeficiency virus

<400> SEQUENCE: 20

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Glu Gly Ile Glu Ile Arg Asp

```
                    85                  90                  95
Thr Lys Glu Ala Leu Asp Lys Ile Glu Glu Gln Asn Lys Ile Gln
                100                 105                 110

Gln Lys Thr Gln Gln Ala Lys Lys Ala Asp Glu Lys Val Ser Gln Asn
            115                 120                 125

Tyr Pro Ile Val Gln Asn Leu Gln Gly Gln Met Val His Gln Ala Ile
130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Val His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Gly Gln Ile Ala Trp Met Thr Ser Asn Pro Pro Val Pro Val Gly
                245                 250                 255

Glu Ile Tyr Lys Arg Trp Ile Ile Leu Gly Leu Asn Lys Ile Val Arg
            260                 265                 270

Met Tyr Ser Pro Val Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Ser Leu Glu Glu Met Met Thr Ala Cys Gln Gly Val Gly Gly
            340                 345                 350

Pro Ser His Lys Ala Arg Val Leu Ala Glu Ala Met Ser Gln Ala Asn
        355                 360                 365

Gly Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Lys Ser Leu Phe Gly Ser Asp Pro Leu Ser Gln
                485                 490

<210> SEQ ID NO 21
```

<211> LENGTH: 1503
<212> TYPE: DNA
<213> ORGANISM: Human immunodeficiency virus

<400> SEQUENCE: 21

| | | | | | |
|---|---|---|---|---|---|
| atgggtgcga | gagcgtcaat | attaagaggg | gaaaaattag | ataaatggga | aagaattagg | 60 |
| ttaaggccag | ggggaaagaa | gcactatatg | ctaaaacacc | tagtatgggc | aagcagggag | 120 |
| ctggacagat | ttgcacttaa | ccctggcctt | ttagaggcag | cagaaggctg | taaacaaata | 180 |
| ataaaacagc | tacaaccagc | tcttcagaca | ggaacagagg | aacttaggtc | attacacaac | 240 |
| acagtagcaa | ctctctattg | tgtacatgaa | gggatagagg | tacgagacac | caaggaagcc | 300 |
| ttagacaaga | tagaggaaga | acaaaacaaa | agtcagcaaa | aaacacagca | ggcaaaagag | 360 |
| gctgacggga | aggtcagtca | aaattatcct | atagtgcaga | atctccaagg | gcaaatggta | 420 |
| caccagccca | tatcacctag | aactttgaat | gcatgggtaa | aagtaataga | ggagaaggct | 480 |
| tttagcccag | aggtaatacc | catgtttaca | gcattatcag | aaggagccac | cccacaagat | 540 |
| ttaaacacca | tgttaaatac | agtagggga | catcaagcag | ccatgcaaat | gttaaaagat | 600 |
| accatcaatg | aagaggctgc | agaatgggat | agattacatc | cagtacatgc | agggcctatt | 660 |
| gcaccaggcc | aaataagaga | accaagggga | agtgacatag | caggaactac | tagtacccttt | 720 |
| caggaacaaa | tagcatggat | gacaggtaac | ccacctgttc | cagtgggaga | catctataaa | 780 |
| agatggataa | ttctggggtt | aaataaaata | gtaagaatgt | atagccctgt | cagcattttg | 840 |
| gacataaaac | aagggccaaa | ggaacccttt | agagactatg | tagaccggtt | ctttagaact | 900 |
| ttaagagctg | aacaagctac | acaagatgta | aaaaattgga | tgacagacac | cttgttggtc | 960 |
| caaaatgcga | acccagattg | taagaccatt | ttaagagcat | tgggaccagg | ggcttcatta | 1020 |
| gaagagatga | tgacagcatg | tcagggagtg | ggaggacctg | gccacaaagc | aagagtgttg | 1080 |
| gctgaggcaa | tgagccaagc | aaacagtaac | atactgatgc | agagaagcaa | ttttaaaggc | 1140 |
| tctaaaagaa | ctgttaaatg | tttcaactgt | ggcaaggaag | gcacatagc | cagaaattgc | 1200 |
| agggccccta | ggaaaaaagg | ctgttggaaa | tgtggaaagg | aaggacacca | aatgaaagac | 1260 |
| tgtactgaga | ggcaggctaa | ttttttaggg | aaaatttggc | cttcccacaa | ggggaggcca | 1320 |
| gggaatttcc | ttcagaacag | accagagcca | acagcccctc | cagccagacc | agagccaaca | 1380 |
| gcccctccag | cagagagctt | caggttcgag | gagacaaccc | ccgctctgaa | gcaggagcca | 1440 |
| aaagacaggg | aacccttaac | ttccctcaaa | tcactctttg | gcagcgaccc | cttgtctcaa | 1500 |
| taa | | | | | | 1503 |

<210> SEQ ID NO 22
<211> LENGTH: 2541
<212> TYPE: DNA
<213> ORGANISM: Human immunodeficiency virus
<220> FEATURE:
<221> NAME/KEY: misc_feature
<222> LOCATION: (222)..(222)
<223> OTHER INFORMATION: n is a, c, g, or t

<400> SEQUENCE: 22

| | | | | | |
|---|---|---|---|---|---|
| atgagagtga | cggggatcag | gaagaactat | cagcatttat | ggagatgggg | caccatgctc | 60 |
| cttgggatgt | tgatgatctg | tagtgctgca | gaaaacttgt | gggtcacagt | ctattatggg | 120 |
| gtacctgtgt | ggaaagaagc | caaaactact | ctattctgtg | cgtcagatgc | taaagcatat | 180 |
| gagaaagaag | tgcataatgt | ctgggctaca | catgcctgtg | tncccacaga | ccccaaccca | 240 |
| caagaaatgg | ttttggaaaa | tgtaacagaa | aattttaaca | tgtggaaaaa | tgacatggtg | 300 |

```
aatcagatgc atgaggatgt aatcagttta tgggatcaaa gcctaaagcc atgtgtaaag    360
ttgaccccac tctgtgtcac tttagaatgt agaaatgtta gcagtaatgg tacctacaat    420
gagacctaca atgagatcaa aaattgctct ttcaatgcaa ccacagtatt aagagatagg    480
aagcagacag tgtatgcact tttttataga cttgatatag taccacttaa taagaagaac    540
tctagtgaga actctagtga gtattataga ttaataaatt gtaataccct cagccataaca    600 caagcctgtc caaggtcac ttttgatcca attcctatac actattgcac tccagctggt     660
tatgcgattc taaagtgtaa tgataagaca ttcaatggaa caggaccatg ccataatgtt    720
agtacagtac aatgtacaca tggaattaag ccagtggtat caactcaact actgttaaat    780
ggtagcctag cagaaagaga gataataatt agatctgaaa atctgacaaa caatgtcaaa    840
acaataatag tacatcttaa tcaatctgta gaaattgtat gtacaagacc caacaataat    900
acaagaaaaa gtataaggat aggaccagga caaacattct atgcaacagg agacataata    960
ggagacataa gacaagcaca ttgtaacatt agtaaagata atggaatga aactttacaa   1020 agggtaggta aaaaattagc agaacacttc cctaataaaa caatagaatt tgcatcatcc   1080
tcaggagggg acctagaaat tacaacacat agctttaatt gtagaggaga attttttctat  1140 tgtaatacat caagcctgtt aatggtaca tacatgccta atggtacaga aggtaattca    1200
agctcaatca tcacaatccc atgcagaata aagcaaatta taaacatgtg gcaggaggta   1260
ggacgagcaa tgtatgcccc tcccattgag ggaaacataa catgtaaatc aaatatcaca   1320
ggactactat tggtacgtga tggaggaaaa gagacaaatg atacagagac attcagacct   1380
ggaggaggag atatgaggga caattggaga agtgaattat ataaatataa agtggtagaa   1440
attaagccat tgggaatagc acccactgca gcaaaaagga gagtggtgga gagagaaaaa   1500
agagcagtgg gaataggagc tgtgttcctt gggttcttgg gagcagcagg aagcactatg   1560
ggcgcggcgt caataacgct gacggtacag gccagacaat tgttgtctgg tatagtgcaa   1620
cagcaaagca atttgctgag ggctatagag gcgcaacagc atctgttgca actcacggtc   1680
tggggcatta agcagctcca gacaagagtc ctggctatag aaagatacct aaaggatcaa   1740
cagctcctag ggatttgggg ctgctctgga aaactcatct gcactactgc tgtacattgg   1800
aactccagtt ggagtaacag atctcaagaa gagatttgga ataacatgac ttggatgcag   1860
tgggatagag aaattagtaa ttacacaaac acaatataca ggttgcttga agactcgcaa   1920
aaccagcagg aaagaaatga aaagatttta ctagcattgg acaattggaa aaatctatgg   1980
agttggtttg acataacaaa ttggctgtgg tatataagaa tattcataat gatagtagga   2040
ggcttgatag gtttaagaat aatttttgct gtgctctcta tagtgaatag agttaggcag   2100
ggatactcac ctttgtcgtt tcagaccctt accccgaacc caggggacc cgacaggctc    2160 ggaagaatcg aagaagaagg tggagagcaa gacaaaaaca gatccattcg attagtgaac   2220
ggattcttag cacttgcctg ggacgacctg cggaacctgt gccgcttcag ctaccacctc   2280
ttgagagact tactcttgat tgtagcaagg attgtggaac ttctgggacg cagggggtgg   2340
gaagccctca gatattggtg gaatctcctg aagtattggg ttcaggaact aaagaatagt   2400
gctgttagtt tgctcaatgc cacagctata gcagtagctg aggggacaga tagggttata   2460
gaagtagtac aaggagctta tagagctatt ctccacatac ctagaagaat aagacagggc   2520
tttgaagcag ctttgcaata a                                             2541
```

<210> SEQ ID NO 23

```
<211> LENGTH: 25
<212> TYPE: DNA
<213> ORGANISM: Artificial
<220> FEATURE:
<223> OTHER INFORMATION: primer

<400> SEQUENCE: 23
ggggattggt tttgacgttt ttgcg                                              25

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
aagcattaaa taaagcgaat acatccttat                                         30

<210> SEQ ID NO 25
<211> LENGTH: 24
<212> TYPE: DNA
<213> ORGANISM: Artificial
<220> FEATURE:
<223> OTHER INFORMATION: labeled, fluorogenic PROBE

<400> SEQUENCE: 25
caattggttt accttttgct cttt                                               24
```

USE OF ALLOGENIC OR SYNGENIC MAJOR HISTOCOMPATIBILITY COMPLEX (MHC) MOLECULES AS UNIVERSAL ADJUVANTS FOR VACCINES AGAINST NEOPLASTIC DISEASE, INFECTION AND AUTOIMMUNE DISEASE

This application claims priority under 35 U.S.C. §119(e) to provisional application No. 60/675,039 filed Apr. 25, 2005, which is incorporated by reference.

1. STATEMENT REGARDING FEDERALLY SPONSORED RESEARCH

The research leading to this invention was supported, in part, by NIH/NIAID Grant No. KO2 AI01682. Accordingly, the United States government may have certain rights to this invention.

2. FIELD OF THE INVENTION

The present invention relates to the use of allogenic or syngenic major histocompatibility complex (MHC) molecules as universal adjuvants to augment the immunogenicity of vaccines against cancer, infectious diseases, allergies, and autoimmune diseases.

3. BACKGROUND OF THE INVENTION

The successful elimination of pathogens, neoplastic cells, or self-reactive immune mechanisms following prophylactic or therapeutic immunization depends to a large extent on the ability of the host's immune system to become activated in response to immunization and to mount an effective response, preferably with minimal injury to healthy tissue.

The rational design of vaccines initially involves identification of immunological correlates of protection—the immune effector mechanism(s) responsible for protection against disease—and the subsequent selection of an antigen that is able to elicit the desired immune response. Once this appropriate antigen has been identified, it is essential to deliver it effectively to the host's immune system.

New vaccines are presently under development and in testing for the control of various neoplastic, autoimmune and infectious diseases. In contrast to older vaccines which were typically based on live-attenuated or non-replicating inactivated pathogens, modern vaccines are composed of synthetic, recombinant, or highly purified subunit antigens. Subunit vaccines are designed to include only the antigens required for protective immunization and are believed to be safer than whole-inactivated or live-attenuated vaccines. However, the purity of the subunit antigens and the absence of the self-adjuvanting immunomodulatory components associated with attenuated or killed vaccines often result in weaker immunogenicity.

For example, DNA vaccination is a novel and potentially powerful approach to prevent and treat disease. The advantages of plasmid DNA immunization, as compared to the traditional protein vaccines, are its abilities to induce T helper 1 (Th1) and CTL responses, the prolonged antigen expression, and the potential long-lived effector activity. Although it is well documented that direct injection of naked DNA encoding different antigens of viral, bacterial, parasitic, and tumor origin can elicit both humoral and cellular immune responses in various animal models, recent results from clinical trials suggest that the immunogenicity of DNA vaccine in humans may be limited. Recently, the use of naked DNA plasmids and recombinant attenuated viruses, such as adenovirus, vaccinia virus and Sindbis virus (Caulfield, et al., *J. Virol.* 2002; 76:10038-10043; Tsuji et al., *J. Virol.* 1998; 72:6907-6910; Rodrigues, et al., *J. Immunol.* 1997; 158:1268-1274), in their single dose or in a priming-boosting strategy (Li et al., *Proc. Natl. Acad. Sci. U SA.* 1993; 90:5214-5218; Amara et al., *J. Virol.* 2002; 76:7625-7631) have been proven to be potent inducers of a pathogen-specific CD8+ T-cell response in animal models. However, the use of recombinant viral vaccines has many disadvantages for practical use in humans. A majority of people worldwide has pre-existing immunity to adenovirus and vaccinia virus that cause impaired immune responses to vaccines, and these viruses are prevalent among human populations. Moreover, the amounts that are required for DNA vaccines in humans are extremely high, i.e. five milligram per dose per person.

Taken together, optimal regimens to enhance the immunogenicity and decrease the required dose of DNA vaccines as well as various subunit vaccines still remain to be established.

3.1. Adjuvants

Among the most established ways for increasing the immunogenicity of antigens is the use of immunoenhancing agents, or "adjuvants". Adjuvants accelerate, prolong, and/or enhance an antigen-specific immune response as well as provide the selective induction of the appropriate type of response. (Ramachandra L, et al., *Immunol. Rev.* 1999; 168: 217-239; Singh M, et al., *Nat. Biotechnol.* 1999; 17:1075-1081). In the absence of an adjuvant, reduced or no immune response may occur, or worse the host may become tolerized to the antigen.

Adjuvants can be found in a group of structurally heterogeneous compounds (Gupta et al., *Vaccine* 1993; 11:293-306). Classically recognized examples of adjuvants include oil emulsions (e.g., Freund's adjuvant), saponins, aluminium or calcium salts (e.g., alum), non-ionic block polymer surfactants, lipopolysaccharides (LPS), mycobacteria, tetanus toxoid, and many others. Theoretically, each molecule or substance that is able to favor or amplify a particular situation in the cascade of immunological events, ultimately leading to a more pronounced immunological response can be defined as an adjuvant.

In principle, through the use of adjuvants in vaccine formulations, one can (1) direct and optimize immune responses that are appropriate or desirable for the vaccine; (2) enable mucosal delivery of vaccines, i.e., administration that results in contact of the vaccine with a mucosal surface such as buccal or gastric or lung epithelium and the associated lymphoid tissue; (3) promote cell-mediated immune responses; (4) enhance the immunogenicity of weaker immunogens, such as highly purified or recombinant antigens; (5) reduce the amount of antigen or the frequency of immunization required to provide protective immunity; and (6) improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms: (1) increasing the biological or immunologic half-life of antigens (see, e.g., Lascelles, *Vet. Immunol. Immunopathol.* 1989; 22: 15-27; Freund, *Adv. Tuber. Res.* 1956; 7: 130-147); (2) improving antigen delivery to antigen-presenting cells (APCs), as well as antigen processing and presentation by the APCs (see, e.g., Fazekas de St. Groth et al., *Immunol. Today,* 1998; 19: 448-454,), e.g., by enabling antigen to cross endosomal membranes into the cytosol after ingestion of antigen-adjuvant complexes by APCs (Kovacsovics-Bankowski et al., *Science*, 1995; 267: 243-246); (3) mimicking microbial structures leading to improved recognition of microbially-derived antigens by the pathogen-recognition receptors (PRRs), which are localized on accessory cells from the innate immune system (Janeway, *Cold Spring Harbor Symp. Quant. Biol.*, 1985; 54:1-13; Medzhitov, *Cell* 1997; 91:295-298; Rook, *Immunol. Today*, 1993; 14:95-96; (4) mimicking danger-inducing signals from stressed or damaged cells which serve to initiate an immune response (see, e.g., Matzinger, *Annu. Rev. Immunol.*, 1994; 12:991-209), (5) inducing the production of immunomodulatory cytokines (see, e.g., Nohria, *Biotherapy*, 1994; 7:261-269; Iwasaki et al., *J. Immunol.* 1997; 158:4591-4601; Maecker et al., *Vaccine* 1997; 15:1687-1696); (6) biasing the immune response towards a specific subset of the immune system (e.g., generating Th1- or Th2-polarized response, etc.) (Janssen et al., *Blood*, 2001; 97:2758-2763; Yamamoto et al., *J. Immunol.* 1999; 53:211-217, 2001; Weiner G. J., *J. Leukoc. Biol.* 2000; 68:455-63; Lucey, *Infect. Dis. Clin. North Am.* 1999; 13:1-9), and (7) blocking rapid dispersal of the antigen challenge (the "depot effect") (Hood et al., *Immunology, Second Ed.*, 1984, Benjamin/Cummings: Menlo Park, Calif.; St Clair et al., *Proc. Natl. Acad. Sci. U.S.A.* 1999; 96:9469-9474; Ahao et al., *J. Pharm. Sci.* 1996; 85:1261-1270; Morein et al., *Vet. Immunol. Immunopathol.* 1996; 54:373-384). (See also reviews by Schijns, *Curr. Opin. Immunol.* 2000; 12: 456-463; Vogel, *Clin. Infect. Dis.* 2000; 30 [Suppl. 3]: S266-70; Singh and O'Hagan, *Nature Biotechnol.* 1999; 17: 1075-81; Cox and Coulter, *Vaccine* 1997; 15: 248-256).

As different adjuvants may have diverse mechanisms of action, their being chosen for use with a particular vaccine may be based on the route of administration to be employed, the type of immune responses desired (e.g., antibody-mediated, cell-mediated, mucosal, etc.), and the particular inadequacy of the primary antigen.

The benefit of incorporating adjuvants into vaccine formulations to enhance immunogenicity must be weighed against the risk that these agents will induce adverse local and/or systemic reactions. Local adverse reactions include local inflammation at the injection site and, rarely, the induction of granuloma or sterile abscess formation. Systemic reactions to adjuvants observed in laboratory animals include malaise, fever, adjuvant arthritis, and anterior uveitis (Allison et al., *Mol. Immunol.* 1991; 28:279-84; Waters et al., *Infect. Immun.* 1986; 51:816-25). Such reactions often are caused by the interaction of the adjuvant and the antigen itself, or may be due to the type of response to a particular antigen the adjuvant produces, or the cytokine profile the adjuvant induces.

Thus, many potent immunoadjuvants, such as Freund's Complete or Freund's Incomplete Adjuvant, are toxic and are therefore useful only for animal research purposes, not human vaccinations. Currently, aluminum salts and MF59 are the only vaccine adjuvants approved for human use but these induce CD8+ T-cell responses poorly. Of the novel adjuvants under evaluation, immunostimulatory molecules such as the lipopolysaccharide-derived MPL and the saponin derivative QS-21 appear most promising, although doubts have been raised as to their safety for human use. Preclinical work with particulate adjuvants, such as the MF59 microemulsion and lipid-particle immuno-stimulating complexes (ISCOMs), suggest that these molecules are also themselves potent elicitors of humoral and cellular immune responses. In addition, preclinical data on CpG oligonucleotides appear to be encouraging, particularly with respect to their ability to manipulate immune responses selectively by causing the activation and stimulation of immune cell (Ramachandra et al., *Immunol. Rev.* 1999; 168:217-239; Singh et al., *Nat. Biotechnol.* 1999; 17:1075-1081), and certain cytokines, such as GM-CSF, IL-12, IFN-γ, IL-15, and IL-18 (Warren et al., *Curr. Opin. Hematol* 2000; 7:168-173; Pasquini et al., 1997; 75:397-401; Lauwerys et al., *J. Immunol* 2000; 165:1847-1853). While some of these adjuvants show promise, the development of more potent novel adjuvants may allow novel vaccines to be developed and both novel and existing vaccines to be used as therapeutic as well as improved prophylactic agents.

3.2. Histocompatibility

The ability to distinguish self from non-self is one of the fundamental functions of the immune system. For example, during an allogenic (i.e., from the same species) tissue or organ transplant, a relatively high frequency of T lymphocytes, which recognize allogenic major histocompatibility complex (allo-MHC) molecules of the graft, are rapidly generated (Ishimoto et al., *J. Immunol* 1997; 159(8): 3717-22). These allo-MHC-reactive T cells initiate a graft-versus-host (GVH) reaction (Martin, *Bone Marrow Transplant* 1990; 6: 283-289). If the graft and host are not "MHC compatible", then the GVH reaction occurs very rapidly and strongly with high efficiency, and the graft normally gets rejected within a day or two. Thus, the allo-reactive T-cell responses are quite detrimental during the GVH reactions.

Two groups of histocompatibility gene products have been identified: "major" and "minor" histocompatibility antigens. "Major histocompatibility antigens" stimulate acute, rapid, intense forms of graft rejection. "Minor histocompatibility antigens" stimulate chronic, slow, less intense reactions (Kobayashi et al., *J. Exp. Med* 1992; 176(2): 617-621).

The genes encoding the histocompatibility antigens responsible for transplantation occur in clusters known as major and minor histocompatibility complexes. Major histocompatibility genes are located on a single chromosome, and the organization of the principal MHC genes is similar in both humans and mice. In humans, major histocompatibility complex (MHC) genes are found on chromosome 6 and designated the HLA complex, whereas in mice the MHC genes are found on chromosome 17 and designated the H-2 complex. Minor histocompatibility genes are scattered throughout the genome. Specifically, there are separate clusters of MHC class I and MHC class II genes. In both species there are three main class I genes, called HLA-A, -B, and -C in humans and H-2K, -D, and -L in mice. The class II region encodes the genes for the α and β chains of the antigen-presenting MHC class II molecules HLA-DR, -DP, and -DQ (I-A and I-E in the mouse).

The MHC plays a physiological role in the presentation of foreign antigen in association with self MHC. "Restriction" refers to the finding that T-cells can only recognize (are "restricted" to recognizing) a foreign antigen only in complex with a self MHC. Thus, CD8 T-cells are self MHC class I-restricted, and CD4 T-cells are self MHC class II restricted.

There are two classes of MHC complexes-class I and class II, and each class is made up of many different alleles. Class I MHC complexes are found on virtually every cell and present peptides from proteins produced inside the cell. Thus, class I MHC complexes are useful for killing cells infected by viruses or cells which have become cancerous as the result of expression of an oncogene. T-cells which have a protein called CD8 on their surface, bind specifically to the MHC class I/peptide complexes via the T-cell receptor (TCR). This leads to cytolytic effector activities. Class II MHC complexes are found only on antigen-presenting cells (APC) and are used to present peptides from circulating pathogens which have been endocytosed by APCs. T-cells which have a protein called CD4 bind to the MHC class II/peptide complexes via TCR. This leads to the synthesis of specific cytokines which stimulate an immune response. To be effectively recognized by the immune system via MHC class I presentation, an antigenic polypeptide has to contain an epitope of at least about 8 to 10 amino acids, while to be effectively recognized by the immune system via MHC class II presentation, an antigenic polypeptide has to contain an epitope of at least about 13 to 25 amino acids. See, e.g., *Fundamental Immunology*, 3rd Edition, W. E. Paul ed., 1999, Lippincott-Raven Publ.

3.2.1. Murine MHC

As inbred strains of mice have the same MHC genes and are homozygous at all gene loci, they are ideal subjects for studying histocompatibility. The murine H-2 gene products or "HMC antigens" primarily (but not exclusively) regulate the processes of transplantation, immune responsiveness and aspects of complement synthesis.

The murine H-2 complex is composed of four major regions (K, I, S, and D). The I region has several subregions, which are divided into eight subdivisions (A, B, J, E, and C). The subregions are also divided into regions (e.g., A=Ab3, Ab2, Ab1, and Aa1). Each region or subregion is believed to contain one locus, but may contain more.

Each gene of the H-2 complex possesses multiple alleles, usually inherited as a block on a given chromosome and designated the "H-2 haplotype". Two haplotypes make up an animal's H-2 genotype. In inbred mice, the two haplotypes are identical. In outbred mice the haplotype may completely or partially differ.

The Tla complex found downstream of the D region also contains several alleles. The Tla gene products are very similar to class I molecules of the H-2 complex and may share in the functions of the H-2 complex.

The four major regions of the H-2 complex encode the following classes of antigens with differing expression patterns. The K and D regions of the H-2 complex encode class I antigens found on all nucleated cells, erythrocytes, and platelets. The I region of the H-2 complex encodes class II antigens, which are found only on B lymphocytes, monocytes, macrophages, epithelial cells, and spermatozoa. The S region encodes the second (C2) and fourth (C4) components of complement, factor B and steroid 21-hydroxylase (21-OHase). (Sackstein R et al., 1984 *Immunogenetics*. 20(3): 321-30). Class III antigens may be formed in, and displayed on, macrophages, and bound, under certain conditions, to lymphocytes, neutrophils, erythrocytes, and platelets. Class III antigens are encoded by the S region, located between the I region that encodes class H antigens and D region that encodes class I antigens.

Most membrane-surface antigens which are exposed to the surface of a cell display a number of epitopes or antigenic determinants. Allo-antigens possess unique epitopes peculiar to their haplotype (private specificities), but they may share epitopes with antigen of other haplotypes (public specificities).

Each haplotype of an inbred strain produces antigens which can stimulate an immune response in strains possessing a haplotype lacking that antigen or unique epitopes within that antigen. This response can be harnessed for use as a adjuvant as seen in this invention.

3.2.1.1. MHC Class I Antigens

The class I antigens are encoded by the genes of the K region and the D Region, with two subregions (D and L), and the Tla region, with 11 subregions (Qa2,3-5, T1, 6-10). Class I antigens are considered classical transplantation antigens: each is a membrane-bound glycoprotein of 45 kDa, consisting of a single peptide chain noncovalently linked to the 12 kD beta2-microglobulin protein. The gene for beta 2-microglobulin is not part of the MHC, but is located on chromosome 2.

Class I antigens encoded by different regions differ in polymorphism and expression. Class I genes encoded by the H-2K and H-2D, L regions encode highly polymorphic cell-surface polypeptides that are found on almost all cell types and are involved in signaling effector T-cells during cell-mediated immunity. However, Class I genes within the Qa and Tla regions exhibit low polymorphism, encode antigen displayed primarily on hemopoietic cells, and are not required for cell-mediated immunity.

Both Class I H2-K and H-2D antigens are strong transplantation antigens capable of provoking strong cell-mediated responses, as well as antibody responses. Recognition of self class I MHC molecules is also required for interaction of cytotoxic T cells with viral infected cells.

Effector T-cells must recognize both the foreign viral antigen and the host MHC antigen during the initiative and destructive phases. Effector T-cells will not destroy cells of a different haplotype infected with the same virus; thus, they exhibit haploytpe-restricted killing. A similar system may be operative in the detection and elimination of transformed cells that must display self-MHC molecules to be destroyed by effector T-cells. This requirement that both the foreign antigen and the host MHC antigen be present is known as MHC restriction.

3.2.1.2. MHC Class II Antigens

Class II antigens are glycoproteins consisting of two non-covalently linked alpha (32 kDa) and beta peptide (28 kDa) chains. Each chain contains two extracellular domains, a connecting peptide, a transmembrane region, and a cytoplasmic tail. The I region of chromosone 17 is divided into five subregions (A, B, J, E, and C) with eight alleles encoding class II antigens.

Antigen-presenting cells (APC) display I region antigen (Ia), in a restricted manner, analogous to MHC restriction. CD4+ T-cells are restricted by class II antigens. CD4+ T-cells normally function as T helper cell, but sometimes as T cytotoxic cells, T suppressor cells or other T-cells, such as regulatory T-cells. Delayed-type hypesensitivity is also controlled in large measure by I region gene products. Thus class II molecules are concerned with recruitment of T helper, T suppressor, and T delayed hypersensitivity cells. Many genes of the I region and their subregions and subdivisions dramatically influence our ability to mount an immune response to an antigen. Consequently, they are referred to as immune response (Ir) genes.

APC or virus-infected cells, present viral antigen in association with self class I molecules, recognized by cytotoxic cells, and class II molecules, recognized by helper cells. Binding of the Class I molecule/viral antigen complex to T cytotoxic cell receptors stimulates expansion of cytotoxic cells. Binding of the class I molecule/viral complex to T helper receptors stimulates expansion of helper cells. The response may be amplified by the release of interleukin 1 from APC and interleukin 2 from both T-cell subsets. T cytotoxic cells will recognize and destroy only target T-cells expressing both self class I molecules and viral antigen.

3.2.1.3. MHC Class III Antigens

Class III genes control the level of C4 proteins, the fourth component of complement, and Slp (sex-linked protein). C4 is a three-chain glycoprotein containing an alpha, beta, gamma chain with molecular weights of 93, 77, and 32 kD, respectively. The Slp locus encodes a sex-linked protein expressed only in males of certain strains of mice.

3.2.2. Major Histocompatibility Complex in Humans (HLA)

Human Leukocyte-Associated (HLA) Antigens are similar to the H-2 complex in mice, containing more than 200 genes. The HLA system was so named because it was discovered through antigenic differences between white blood cells from different individuals. The HLA system in humans is of critical interest to organ transplantation, and attempts were made to identify and match donor antigens as closely as possible with those of the recipient.

There are three class I α chain genes in humans, called HLA-A, -B, and -C. There are also three pairs of MHC class II α- and β-chain genes, called HLA-DR, -DP, and -DQ. In many cases, the HLA-DR cluster contains an extra β-chain gene whose product can pair with the DRα chain. Thus, the three sets of genes can give rise to 4 types of MHC class II molecules. Class III genes encode various other proteins with functions in the immune system, but do not take part in antigen presentation. All of the MHC class I and II molecules can present peptides to T-cells, but each protein binds a different range of peptides.

The HLA-DM genes coding for the DM molecule whose function is to catalyze peptide binding to the MHC class II molecules are related to the MHC class II genes. Likewise, the DNα and DOβ genes, which encode the DO molecule, a negative regulator of DM, are related to the MHC class II genes.

Taken together, there is a great need in the art to develop novel more efficient ways to enhance antigen-specific immune responses and in this way develop more potent vaccines and treatments. The present invention satisfies this and other needs by providing a new type of adjuvants.

4. SUMMARY OF THE INVENTION

The present invention takes advantage of the allo-reactive and auto-reactive acute cellular responses as a means to enhance antigen-specific immune responses. While it is conventionally believed that local inflammation caused by adjuvant administration is an undesirable effect, the present inventors have determined that a controlled stimulation of the host's allogenic or syngenic inflammatory response can be helpful in promoting vaccine efficacy. Specifically, as disclosed herein, allogenic or syngenic adjuvant stimulation can cause local inflammation which increases the antigen presentation capability of cells in the vicinity of adjuvant stimulation. By discovering this phenomenon, the present invention provides a novel method for augmenting the immunogencity of an antigen by co-administering an allogenic or syngenic MHC molecule (as a universal adjuvant) to trigger a local inflammatory reaction to enhance antigen presentation at the site of delivery.

One object of the present invention is to provide a method for augmenting an immune response to an antigen in a mammal comprising conjointly administering to said mammal: (i) an antigen in a first amount, and (ii) an allogenic or syngenic MHC molecule in a second amount; said first and second amounts being effective in combination to augment the immune response mounted against said antigen by the mammal, as compared to the immune response that the mammal could have mounted upon the administration of said first amount of said antigen without the conjoint administration of said MHC molecule.

To be administered conjointly, the MHC-based adjuvant and antigen can be administered either sequentially within 24 hours of each other, or, more preferably, simultaneously. In a preferred embodiment, the MHC-based adjuvant and antigen are also administered at the same site, e.g., within about one inch of each other, most preferably, in the same final composition.

Preferred routes of administration according to the present invention are intramuscular, intradermal, intranasal, subcutaneous, and oral.

According to the present invention, a preferred immunogenically effective amount of the antigen is in the range of 0.01 mg-1 mg per kg of body weight, and a preferred immunogenically effective amount of allogenic or syngenic MHC molecule is in the range of 0.01 mg-0.1 mg per kg of body weight.

The method of the invention can be practiced in any mammal. In a specific embodiment, the mammal is human.

Allogenic and syngenic MHC molecules useful in the method of the invention are either MHC class I molecules or MHC class II molecules. Preferably, allogenic MHC molecules useful as universal adjuvants in the method of the present invention are MHC molecules which are not frequently found in a given animal or human population. Non-limiting examples of murine allo-MHC molecules useful for augmenting an immune response to an antigen in mice include H2-K, H-2D, H2-L, H2-IA, H2-IB, H2-IJ, H2-IE, H2-IC. Non-limiting examples of human allo-MHC class I molecules useful for augmenting an immune response to an antigen in humans include HLA-A*43, HLA-A*69, HLA-A*80, HLA-B*59, HLA-B*81, HLA-B*82, HLA-Cw*14, and HLA-Cw*18. Non-limiting examples of human allo-MHC class II molecules useful for augmenting an immune response to an antigen in humans include HLA-DRB1*16, HLA-DQA1*06, HLA-DPA1*04, HLA-DPB1*33 and HLA-DPB1*41.

According to the present invention, the antigen can be any molecule including, without limitation, proteins, peptides, polysaccharides, glycoproteins, glycolipids, nucleic acids, and any combination thereof. In a specific embodiment, the antigen is presented by a recombinant virus expressing said antigen. Preferably, the virus is selected from the group consisting of a recombinant adenovirus, recombinant pox virus, and recombinant Sindbis virus.

The antigens useful in the methods and compositions of the present invention include without limitation various viral, bacterial, fungal, parasite-specific, tumor-specific, and autoimmune disease-specific antigens.

In a specific embodiment, an antigen or an MHC molecule or both are encoded by an expression vector. In a preferred embodiment, the expression vector is an adenovirus vector, modified vaccinia Ankara vector, pVAX plasmid vector, pVR1012 plasmid vector, or pTHr plasmid vector. An antigen and an MHC molecule can be encoded by the same or different expression vectors. The expression of an antigen and an MHC molecule from the same expression vector can be controlled by one, two, or three promoters. Non-limiting examples of promoters useful for expression of MHC molecules include EXV-3, CMV, HEF-1α, and Rous sarcoma virus (RSV) promoters. In one embodiment, the expression of an antigen and an MHC molecule from the same expression vector results in the production of a fusion protein comprising both the antigen and the MHC molecule. In another embodiment, the expression of an antigen and an MHC molecule from the same expression vector results in the production of two different proteins.

In a specific embodiment, the present invention discloses a method for augmenting an immune response to a sporozoite stage of malaria in a susceptible mammalian host comprising conjointly administering to said host: (i) at least one malaria-specific antigen in a first amount, and (ii) an allogenic or syngenic MHC molecule in a second amount, said first and second amounts being effective in combination to augment the immune response mounted against said antigen by the host, as compared to the immune response that the host could have mounted upon the administration of said first amount of said antigen without the conjoint administration of said MHC molecule. A preferred malaria-specific antigen according to the invention comprises irradiated plasmodial sporozoites or a synthetic peptide antigen comprising a T cell epitope of the malarial circumsporozoite (CS) protein.

In another specific embodiment, the present invention provides a method for augmenting an immune response to an HIV antigen in a susceptible mammalian host comprising conjointly administering to said host: (i) at least one HIV-specific antigen in a first amount, and (ii) an allogenic or syngenic MHC molecule in a second amount, said first and second amounts being effective in combination to augment the immune response mounted against said antigen by the host, as compared to the immune response that the host could have mounted upon the administration of said first amount of said antigen without the conjoint administration of said MHC molecule. A preferred HIV-specific antigen according to the invention comprises a T cell epitope of Gag, Tat, Pol, Env, Nef, gp160, p18, and gp120.

In conjunction with the above-identified method, the present invention also provides a prophylactic and/or therapeutic method for treating a disease in a mammal comprising conjointly administering to said mammal: (i) an antigen associated with the disease in a first amount, and (ii) an allogenic or syngenic MHC molecule in a second amount, said first and second amounts being immunogenically effective in combination.

As specified herein, this method can be useful for preventing and/or treating various infectious, neoplastic and autoimmune diseases including allergies and asthma. Non-limiting examples of infectious diseases that can be treated using the method of the invention include viral infections, bacterial infections, parasitic infections, and fungal infections. Non-limiting examples of neoplastic diseases that can be treated using the method of the invention include solid or blood tumors such as sarcomas, carcinomas, gliomas, blastomas, pancreatic cancer, breast cancer, ovarian cancer, prostate cancer, lymphoma, leukemia, and melanoma. Non-limiting examples of autoimmune diseases that can be treated using the method of the invention include rheumatoid arthritis, insulin-dependent diabetes mellitus, autoimmune thyroiditis, multiple sclerosis, uveoretinitis, lupus erythematosus, scleroderma, allergy and asthma.

In conjunction with the methods disclosed herein, the present invention also provides immunogenic compositions comprising an immunogenically effective amount of (i) an antigen and (ii) an allogenic or syngenic MHC molecule.

In a related embodiment, the present invention provides a kit for the preparation of an immunogenic composition comprising at least one antigen and an allogenic or syngenic MHC molecule, and optionally instructions for admixing the antigen and MHC molecule and/or for administration of the composition.

In another aspect, the present invention provides a method for preparing an immunogenic composition comprising at least one antigen and an allogenic or syngenic MHC molecule, said method comprising admixing the antigen with the MHC molecule and optionally with one or more pharmaceutically acceptable carriers.

The present invention also provides a method for preparing an immunogenic composition comprising an expression vector encoding at least one antigen and an allogenic or syngenic MHC molecule, said method comprising admixing the expression vector with one or more pharmaceutically acceptable carriers.

Furthermore, the present invention provides a method for preparing an immunogenic composition comprising a first expression vector encoding at least one antigen and a second expression vector encoding an allogenic or syngenic MHC molecule, said method comprising admixing the first expression vector with the second expression vector and optionally with one or more pharmaceutically acceptable carriers.

5. BRIEF DESCRIPTION OF THE DRAWINGS

FIG. 1 is a graph showing CS-specific T cell responses after subcutaneous (s.c.) co-administration to BALB/c mice (H-$2^d$ haplotype) of (i) a sub-optimal dose of a recombinant adenovirus expressing *P. yoelii* CS protein (AdPyCS) and (ii) syngenic BALB/c splenocytes (H-$2^d$ haplotype) or allogenic C57BL/6 (B6) splenocytes (H-$2^b$ haplotype) or xenogenic human peripheral blood lymphocytes (PBLs). Mice immunized with AdPyCS alone ("None") were used as a control. The CS-specific T cell responses were measured by the numbers of IFN-γ-secreting CS-specific CD4+ and CD8+ T cells as determined using an ELISPOT assay. Increased CS-specific T-cell responses were observed upon co-administration of AdPyCS with syngenic BALB/c splenocytes (H-$2^d$ haplotype) and allogenic C57BL/6 (B6) splenocytes (H-$2^b$ haplotype), but not upon co-administration of AdPyCS with xenogenic human peripheral blood lymphocytes (PBLs).

Figure 2:
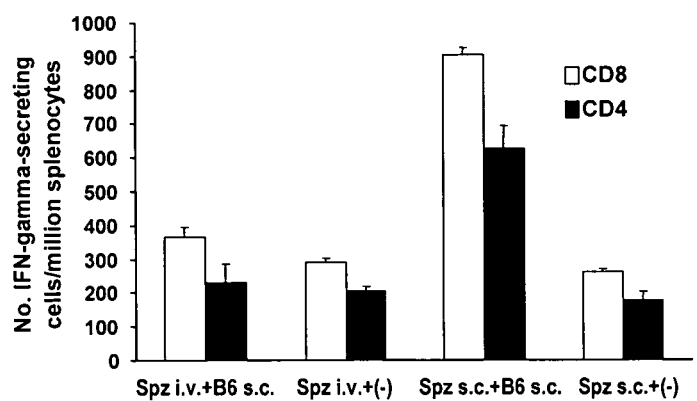

FIG. 2 is a graph showing the effect of a route of administration on the increase in CS-specific T cell responses produced by co-administration to BALB/c mice (H-$2^d$ haplotype) of (i) a sub-optimal dose of irradiated *P. yoelii* sporozoites ("Spz") and (ii) allogenic C57BL/6 splenocytes (H-$2^b$ haplotype) ("B6"). Mice immunized with Spz alone ("(−)") were used as a control. Immunization was either by subcutaneous ("s.c.") or intravenous ("i.v.") routes. The CS-specific T cell responses were measured by the numbers of IFN-γ-secreting CS-specific CD4+ and CD8+ T cells as determined using an ELISPOT assay. Highly increased CS-specific T-cell responses were observed upon subcutaneous co-administration of Spz with syngenic BALB/c splenocytes, but not upon intravenous co-administration.

Figure 3:
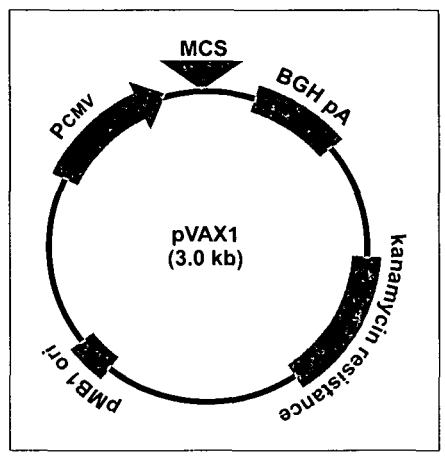

FIG. 3 is a schematic map of pVAX1, a commercially-available plasmid from Invitrogen® (Catalogue No. V260-20). pVAX1 is specifically designed for use in the development of DNA vaccines. The plasmid contains eukaryotic DNA sequences limited to those required for expression in order to minimize the possibility of chromosomal integration. The plasmid also contains the kanamycin resistance gene for selection in E. coli, a multiple cloning site (MCS), a CMV promoter, a pMB1 bacterial origin of replication, and a BGH pA (bovine growth hormone polyadenylation site).

Figure 4:
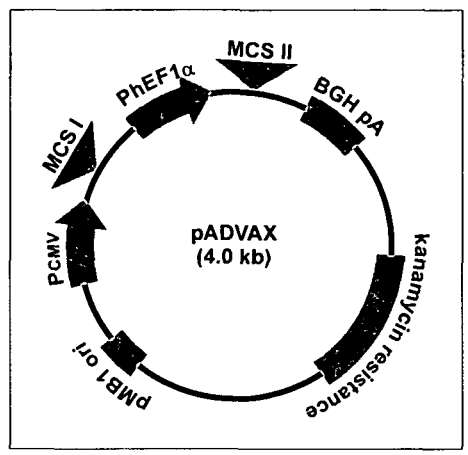

FIG. 4 is a schematic map of the pADVAX plasmid. pADVAX is a modification of pVAX1 which was created by the insertion of an additional promoter, the human elongation factor 1α (hEF1α) promoter from pBudCE4.1, a commercially-available vector (Invitrogen®, Catalogue No. V532-20). The promoter was cloned into the EcoR1/Not1 sites of pVAX1 and verified with sequencing. The plasmid also contains two multiple cloning sites (MCS I and MCS II). This alteration of pVAX1, yielding pADVAX, permits independent, high-level expression of a second genetic insert.

Figure 5:
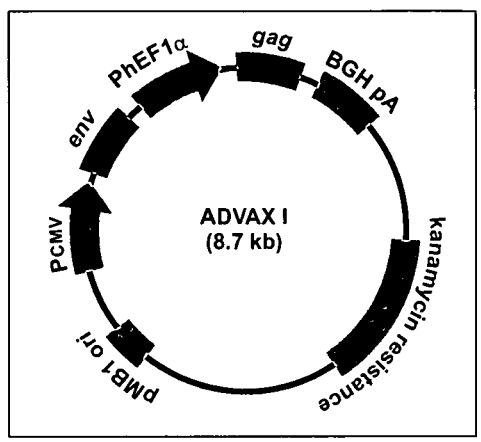

FIG. 5 is a schematic map of the ADVAX1 vaccine. The ADVAX1 vaccine is based on the pADVAX plasmid and contains HIV-1 env and gag genes. Production of the ADVAX1 vaccine is described in Example 3. infra.

Figure 6:
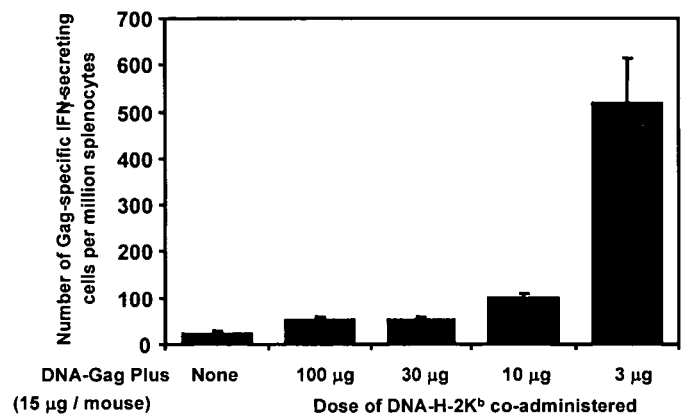

FIG. 6 is a graph showing Gag-specific CD8+ T cell responses after intramuscular (i.m.) co-administration to BALB/c mice ($H-2^d$ haplotype) of (i) a sub-optimal dose of pVAX plasmid encoding HIV-Gag (ADVAX1) and (ii) different doses, ranging from 3 µg to 100 µg, of pVAX plasmid encoding the allogenic MHC molecule $H-2K^b$ (pVAX-H-$2K^b$). Mice immunized with ADVAX1 alone ("None") were used as a control. The Gag-specific CD8+ T cell responses were measured by the numbers of IFN-γ-secreting Gag-specific CD8+ T cells as determined using an ELISPOT assay. Co-administration of ADVAX1 with 3 µg of pVAX-H-$2K^b$ enhanced the number of Gag-specific CD8+ T-cell responses approximately 20-fold, as compared to that elicited by ADVAX1 immunization alone.

Figure 7:
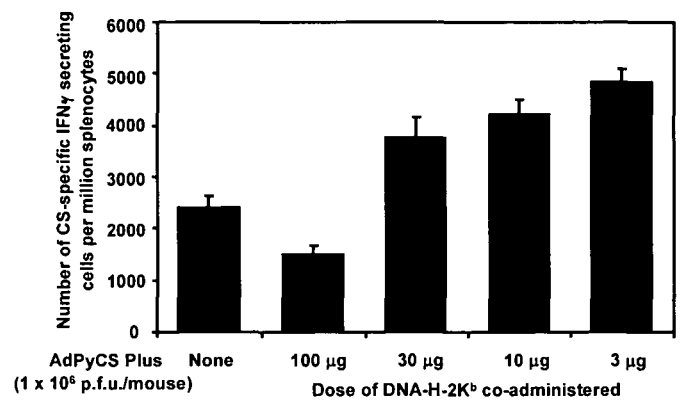

FIG. 7 is a graph showing CS-specific CD8+ T cell responses after intramuscular (i.m.) co-administration to BALB/c mice ($H-2^d$ haplotype) of (i) a sub-optimal dose of a recombinant adenovirus expressing P. yoelii CS protein (AdPyCS) and (ii) different doses, ranging from 3 µg to 100 µg, of pVAX plasmid encoding the allogenic MHC molecule $H-2K^b$ (pVAX-H-$2K^b$). Mice immunized with AdPyCS alone ("None") were used as a control. The CS-specific CD8+ T cell responses were measured by the numbers of IFN-γ-secreting CS-specific CD8+ T cells as determined using an ELISPOT assay. Co-administration of AdPyCS with 3 µg of pVAX-H-$2K^b$ enhanced the number of CS-specific CD8+ T-cell responses approximately 2-fold, as compared to that elicited by AdPyCS immunization alone.

6. DETAILED DESCRIPTION OF THE INVENTION

The present invention takes advantage of the allo-reactive and auto-reactive acute cellular responses as a means to enhance antigen-specific immune responses. As disclosed herein, allogenic or syngenic adjuvant stimulation can cause local inflammation which increases the antigen presentation capability of cells in the vicinity of adjuvant stimulation. By discovering this phenomenon, the present invention provides a novel method for augmenting the immunogencity of an antigen by conjointly administering an allogenic or syngenic MHC molecule (as a universal adjuvant) to trigger a local inflammatory reaction to enhance antigen presentation at the site of delivery. For example, as demonstrated in the Examples section, infra, allogenic and syngenic MHC molecules can significantly enhance antigen-specific T cell-mediated immune responses to malarial and HIV antigens upon subcutaneous or intramuscular co-administration to mice.

Conjoint administration of the MHC-based adjuvant induces an acute T cell response/cytokine production (generally within 48 hours) and increases both the length and the strength of the T cell response. Allogenic MHC molecules induce allo-reactive T cell responses, while syngenic MHC molecules induce auto-reactive T cell responses. As disclosed herein, both MHC class I and MHC class II molecules are useful as universal adjuvants of the present invention, with MHC class I inducing primarily CTL/CD8+ T cell responses, and MHC class II inducing primarily CD4+ T cell responses.

6.3. Definitions

The terms "adjuvant" and "immunoadjuvant" are used interchangeably in the present invention and refer to a compound or mixture that augments the host's immune response to another antigen when administered conjointly with that antigen.

Adjuvant-mediated enhancement and/or extension of the duration of the antigen-specific immune response can be assessed by any method known in the art including, without limitation, an increase in the number of T-cells recognizing the antigen and an increase in the level of one or more cytokines.

Adjuvants of the invention comprise either allogenic or syngenic histocompatibility molecules. The terms "histocompatibility" or "MHC" or "HLA" are used herein to describe the genetic systems that determine the rejection of tissue and organ grafts resulting from immunological recognition of histocompatibility molecules. The MHC class I molecules present peptides generated in the cytosol to CD8+ T-cells, and the MHC class II molecules present peptides degraded in intracellular vesicles to CD4+ T-cells. "Histocompatibility molecules" are defined herein as the set of expressed membrane glycoproteins called the "MHC molecules" or the "MHC antigens" or the "major histocompatibility molecules" or "major histocompatibility antigens" that are recognized by the recipient as self or non-self.

These molecules are encoded by the "major histocompatibility complex" or "MHC", a cluster of genes on human chromosome 6 or mouse chromosome 17. In humans, "HLA" or "Human Leukocyte Antigen" are the histocompatibility antigens. Individual loci are designated by upper-case letters and alleles are designated by numbers. In mice "H-2" gene products or the "H-2 complex" are the MHC antigens. The H-2 complex is composed of four major regions (K, I, S, and D). The I region has several subregions, which are divided into eight subdivisions (A, B, J, E, and C). The subregions are also divided into regions (e.g., A=Ab3, Ab2, Ab1, and Aa1). Each region or subregion is believed to contain one locus, but may contain more.

Within the meaning of the present invention, the term "allogenic" (or "allo" used as a prefix) refers to a gene, protein, cell, or tissue (e.g., MHC) which is non-self but from the same species. For example, an MHC molecule $H-2K^b$ or a C57BL/6 splenocyte ($H-2^b$ haplotype) are allogenic when administered to BALB/c mice ($H-2^d$ haplotype). An "allograft" is a graft of tissue from an allogenic or non-self donor of the same species. The term "syngenic" (or "auto" used as a prefix) refers to a gene, protein, cell, or tissue (e.g., MHC) which is self or identical to it. For example, an MHC molecule $H-2K^d$ or a BALB/c splenocyte (H-2d haplotype) are allogenic when administered to BALB/c mice ($H-2^d$ haplotype). The term "xenogenic" (or "xeno" used as a prefix) refers to a gene, protein, cell, or tissue (e.g., MHC) which is non-self and from different species. For example, human MHC molecules (HLAs) or human peripheral blood lymphocytes (PBLs) are xenogenic when administered to mice. A "xenograft" is a graft from one species to another.

Within the meaning of the present invention, the term "conjoint administration" is used to refer to administration of an immune adjuvant and an antigen simultaneously in one composition, or simultaneously in different compositions, or sequentially within a 24 hour period.

Within the meaning of the present invention, the term "same site" of administration is used to refer to administering an antigen and an MHC molecule up to and including about one inch apart from each other.

As used herein, the term "native antibodies" or "immunoglobulins" refers to usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain (VL) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 1985; 186: 651-663; Novotny and Haber, *Proc. Natl. Acad. Sci. USA* 1985; 82: 4592-4596).

The term "antibody" or "Ab" is used in the broadest sense and specifically covers not only native antibodies but also single monoclonal antibodies (including agonist and antagonist antibodies), antibody compositions with polyepitopic specificity, as well as antibody fragments (e.g., Fab, $F(ab')_2$ $scF_v$ and $F_v$, so long as they exhibit the desired biological activity.

The term "subject" as used herein refers to an animal having an immune system, preferably a mammal (e.g., rodent such as mouse). In particular, the term refers to humans.

As used herein, the term "immunogenic" means that an agent is capable of eliciting a humoral or cellular immune response, and preferably both. An immunogenic entity is also antigenic. An immunogenic composition is a composition that elicits a humoral or cellular immune response, or both, when administered to an animal having an immune system. The term "antigen" refers to any agent (e.g., protein, peptide, polysaccharide, glycoprotein, glycolipid, nucleic acid, or combination thereof) that, when introduced into a host, animal or human, having an immune system (directly or upon expression as in, e.g., DNA vaccines), is recognized by the immune system of the host and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T-cell antigen receptor (TCR). Within the meaning of the present invention, the antigens are preferably "surface antigens", i.e., expressed naturally on the surface of a pathogen, or the surface of an infected cell, or the surface of a tumor cell. A molecule that is antigenic need not be itself immunogenic, i.e., capable of eliciting an immune response without an adjuvant or carrier.

The term "epitope" or "antigenic determinant" refers to any portion of an antigen recognized either by B cells, or T-cells, or both. Preferably, interaction of such epitope with an antigen recognition site of an immunoglobulin (antibody) or T-cell antigen receptor (TCR) leads to the induction of antigen-specific immune response. T-cells recognize proteins only when they have been cleaved into smaller peptides and are presented as a complex with MHC molecules located on another cell's surface.

The term "malaria-derived" or "malaria-specific" antigen refers to a natural (e.g., irradiated sporozoites) or synthetic (e.g., chemically produced multiple antigen peptide [MAP] or recombinantly synthesized polypeptide) antigen comprising at least one epitope (B cell and/or T-cell) derived from any one of the proteins constituting plasmodium (said plasmodium being without limitation *P. falciparum, P. vivax, P. malariae, P. ovale, P. reichenowi, P. knowlesi, P. cynomolgi, P. brasilianum, P. yoelii, P. berghei,* or *P. chabaudi*) and comprising at least 5-10 amino acid residues. A preferred plasmodial protein for antigen generation is circumsporozoite (CS) protein, however, other proteins can be also used, e.g., Thrombospondin Related Adhesion (Anonymous) protein (TRAP), also called Sporozoite Surface Protein 2 (SSP2), LSA I, hsp70, SALSA, STARP, Hep17, MSA, RAP-1, RAP-2, etc.

The term "vaccine" refers to a composition (e.g., a protein or vector such as, e.g., an adenoviral vector, Sindbis virus vector, recombinant yellow fever virus, recombinant dengue virus or pox virus vector) that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs). Vaccine efficacy can be established in animal models.

The term "DNA vaccine" is an informal term of art, and is used herein to refer to a vaccine delivered by means of a recombinant vector. An alternative, and more descriptive term used herein is "vector vaccine" (since some potential vectors, such as retroviruses and lentiviruses are RNA viruses, and since in some instances non-viral RNA instead of DNA is delivered to cells through the vector).

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease. The term "protect" is used herein to mean prevent or treat, or both, as appropriate, development or continuance of a disease in a subject. Preferably, the disease is either infectious disease (e.g., viral, bacterial, parasitic, or fungal), malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.), or an autoimmune disorder (e.g., rheumatoid arthritis, insulin-dependent diabetes mellitus, autoimmune thyroiditis, multiple sclerosis, uveoretinitis, lupus erythematosus, scleroderma, allergy and asthma).

The term "protective immunity" refers to an immune response in a host animal (either active/acquired or passive/innate, or both) which leads to inactivation and/or reduction in the load of said antigen and to generation of long-lasting immunity (that is acquired, e.g., through production of antibodies), which prevents or delays the development of a disease upon repeated exposure to the same or a related antigen. A "protective immune response" comprises a humoral (antibody) immunity or cellular immunity, or both, effective to, e.g., eliminate or reduce the load of a pathogen or infected cell (or produce any other measurable alleviation of the infection), or to reduce a tumor burden in an immunized (vaccinated) subject.

Immune systems are classified into two general systems, the "innate" or "natural" immune system and the "acquired" or "adaptive" immune system. It is thought that the innate immune system initially keeps the infection under control, allowing time for the adaptive immune system to develop an appropriate response. Recent studies have suggested that the various components of the innate immune system trigger and augment the components of the adaptive immune system, including antigen-specific B and T lymphocytes (Fearon and Locksley, supra; Kos, *Immunol. Res.,* 1998; 17: 303; Romagnani, *Immunol. Today* 1992; 13: 379; Banchereau and Steinman, *Nature* 1988; 392: 245).

The term "innate immunity" or "natural immunity" refers to innate immune responses that are not affected by prior contact with the antigen. Cells of the innate immune system, including macrophages and dendritic cells (DC), take up foreign antigens through pattern recognition receptors, combine peptide fragments of these antigens with MHC class I and class II molecules, and stimulate naive CD8+ and CD4+ T-cells respectively (Banchereau and Steinman, supra; Holmskov et al., *Immunol. Today,* 1994; 15: 67; Ulevitch and Tobias, *Annu. Rev. Immunol.* 1995; 13: 437). Professional antigen-presenting cells (APC) communicate with these T-cells leading to the differentiation of naive CD4+ T-cells into T-helper 1 (Th1) or T-helper 2 (Th2) lymphocytes that mediate cellular and humoral immunity, respectively (Trinchieri, *Annu. Rev. Immunol.* 1995; 13: 251; Howard and O'Garra, *Immunol. Today* 1992; 13: 198; Abbas et al., *Nature* 1996; 383: 787; Okamura et al., *Adv. Immunol.* 1998; 70: 281; Mosmann and Sad, *Immunol. Today* 1996; 17: 138; O'Garra, *Immunity* 1998; 8: 275).

The term "acquired immunity" or "adaptive immunity" is used herein to mean active or passive, humoral or cellular immunity that is established during the life of an animal, is specific for the inducing antigen, and is marked by an enhanced response on repeated encounters with said antigen. A key feature of the T lymphocytes of the adaptive immune system is their ability to detect minute concentrations of pathogen-derived peptides presented by MHC molecules on the cell surface.

As used herein, the term "augment an immune response" or "augment an immunogenicity" refers to enhancing or extending the duration of an immune response, or both. When referred to a property of an agent (e.g., an adjuvant), the term "[able to] augment the immunogenicity of an antigen" refers to the ability to enhance the immunogenicity of an antigen or the ability to extend the duration of the immune response to an antigen, or both.

The phrase "enhance immune response" within the meaning of the present invention refers to the property or process of increasing the scale and/or efficiency of immunoreactivity to a given antigen. When used in reference to the MHC-based adjuvants of the invention, said immunoreactivity is preferably a cellular immunity, most preferably CD4+ and/or CD8+ T cell-mediated immunity. An immune response is believed to be enhanced, if any measurable parameter of antigen-specific immunoreactivity (e.g., T-cell production) is increased at least two-fold, preferably ten-fold, most preferably thirty-fold.

The term "therapeutically effective" applied to dose or amount refers to that quantity of a compound or pharmaceutical composition or vaccine that is sufficient to result in a desired activity upon administration to a mammal in need thereof. As used herein with respect to MHC-based adjuvant- and antigen-containing compositions or vaccines, the term "therapeutically effective amount/dose" is used interchangeably with the term "immunogenically effective amount/dose" and refers to the amount/dose of a compound (e.g., an antigen and/or an MHC molecule) or pharmaceutical composition or vaccine that is sufficient to produce an effective immune response upon administration to a mammal. According to the present invention, a preferred immunogenically effective amount of the antigen is in the range of 0.01 mg-1 mg per kg of body weight, and a preferred immunogenically effective amount of allogenic or syngenic MHC molecule is in the range of 0.01 mg-0.1 mg per kg of body weight.

The phrase "pharmaceutically acceptable", as used in connection with compositions of the invention, refers to molecular entities and other ingredients of such compositions that are physiologically tolerable and do not typically produce unwanted reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical or vaccine compositions of the invention refers to a diluent, excipient, or vehicle with which a compound (e.g., an antigen and/or an MHC molecule) is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The term "about" or "approximately" usually means within 20%, more preferably within 10%, and most preferably still within 5% of a given value or range. Alternatively, especially in biological systems (e.g., when measuring an immune response), the term "about" means within about a log (i.e., an order of magnitude) preferably within a factor of two of a given value.

The terms "vector", "cloning vector", and "expression vector" mean the vehicle by which a DNA or RNA sequence (e.g., a foreign gene) can be introduced into a host-cell. These vehicles may also promote expression (e.g., transcription and/or translation) of the introduced sequence in a host cell. Vectors include plasmids, phages, viruses, etc.

In accordance with the present invention, conventional molecular biology, microbiology, and recombinant DNA techniques may be employed within the skill of the art. Such techniques are well-known and are explained fully in the literature. See, e.g., Sambrook, Fritsch and Maniatis, *Molecular Cloning: A Laboratory Manual,* Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); *Oligonucleotide Synthesis* (M. J. Gait ed. 1984); Nucleic Acid Hybridization [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

A "nucleic acid molecule" (or alternatively "nucleic acid") refers to the phosphate ester polymeric form of ribonucleosides (adenosine, guanosine, uridine, or cytidine: "RNA molecules") or deoxyribonucleosides (deoxyadenosine, deoxyguanosine, deoxythymidine, or deoxycytidine: "DNA molecules"), or any phosphoester analogs thereof, such as phosphorothioates and thioesters, in either single stranded form, or a double-stranded helix. Oligonucleotides (having fewer than 100 nucleotide constituent units) or polynucleotides are included within the defined term as well as double stranded DNA-DNA, DNA-RNA, and RNA-RNA helices. This term, for instance, includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell. Generally, a DNA sequence encoding a particular protein or enzyme is "transcribed" into a corresponding sequence of mRNA. The mRNA sequence is, in turn, "translated" into the sequence of amino acids which form a protein. An "amino acid sequence" is any chain of two or more amino acids. The term "peptide" is usually used for amino acid-based polymers having fewer than 100 amino acid constituent units, whereas the term "polypeptide" is reserved for polymers having at least 100 such units. Herein, however, "polypeptide" will be the generic term.

6.4. Use of Allogenic and Syngenic MHC-based Adjuvants of the Invention

In one aspect, the present invention provides a method for augmenting an immune response to an antigen in a mammal comprising conjointly administering to said mammal: (i) an antigen in a first amount, and (ii) an allogenic or syngenic MHC molecule in a second amount; said first and second amounts being effective in combination to augment the immune response mounted against said antigen by the mammal, as compared to the immune response that the mammal could have mounted upon the administration of said first amount of said antigen without the conjoint administration of said MHC molecule.

The immunostimulating effects of allogenic and syngenic MHC molecules in mammals depend on their ability to cause local inflammation to enhance antigen presentation capability. Indeed, the instant invention demonstrates that the adjuvant activity derived from allogenic and syngenic MHC molecules is attributed at least in part to their ability to enhance antigen-specific CD4+ and CD8+ T-cell responses.

From an immunotherapy view point, the use of allogenic or syngenic MHC molecules to mediate activation of the immune system appears to have distinct advantages as local administration of the MHC molecule will minimize inflammation, the allogenic or syngenic MHC molecules will quickly be cleared from the system, and the transient inflammatory response will effectively stimulate antigen presenting cells (APC) of the vaccine antigen. Moreover, when vectors expressing allogenic MHC molecules are used, there would be no concern for the foreign gene integration into the host genome, because allo-antigens are highly immunogenic and the cells carrying the allo-antigens should be immediately eliminated.

According to the present invention, an adjuvant comprising an allogenic or syngenic MHC molecule and an antigen (or vectors expressing such molecules) can be administered either as two separate formulations or as part of the same formulation. If administered as two separate formulations, the MHC molecule and antigen are administered conjointly, i.e., either sequentially within 24 hours of each other or simultaneously. Simultaneous administration of allogenic or syngenic MHC molecules with an antigen is preferred and generally allows to achieve the most efficient immunostimulation.

In a preferred embodiment, the MHC-based adjuvant and antigen are also administered at the same site within about one inch of each other, most preferably, in the same final composition.

According to the present invention, preferred routes of administration for an antigen and an MHC-based adjuvant are intramuscular (i.m.), intradermal (i.d.), intranasal, subcutaneous (s.c.), and oral. Thus, as disclosed in Example 2, infra, highly increased CS-specific CD4+ and CD8+ T cell responses were observed upon subcutaneous (s.c.) co-administration to BALB/c mice (H-$2^d$ haplotype) of (i) a sub-optimal dose of irradiated *P. yoelii* sporozoites and (ii) allogenic C57BL/6 splenocytes (H-$2^b$ haplotype), but not upon their intravenous (i.v.) co-administration.

According to the present invention, a preferred immunogenically effective amount of the antigen is in the range of 0.01 mg-1 mg per kg of body weight, and a preferred immunogenically effective amount of allogenic or syngenic MHC-based adjuvant is in the range of 0.01 mg-0.1 mg per kg of body weight.

The method of the invention can be practiced in any mammal. In a specific embodiment, the mammal is human.

Allogenic and syngenic MHC molecules useful in the method of the invention are either MHC class I molecules or MHC class II molecules. Preferably, allogenic MHC molecules useful as universal adjuvants in the method of the present invention are MHC molecules which are not frequently found in a given animal or human population. Non-limiting examples of murine allo-MHC molecules useful for augmenting an immune response to an antigen in mice include H2-K, H-2D, H2-L, H2-IA, H2-IB, H2-IJ, H2-IE, H2-IC. Non-limiting examples of human allo-MHC class I molecules useful for augmenting an immune response to an antigen in humans include HLA-A*43, HLA-A*69, HLA-A*80, HLA-B*59, HLA-B*81, HLA-B*82, HLA-Cw*14, and HLA-Cw*18. Non-limiting examples of human allo-MHC class II molecules useful for augmenting an immune response to an antigen in humans include HLA-DRB1*16, HLA-DQA1*06, HLA-DPA1*04, HLA-DPB1*33 and HLA-DPB1*41.

In another aspect, the present invention encompasses the use of multiple allogenic MHC molecules, multiple syngenic MHC molecules, or combinations of allogenic and syngenic MHC molecules.

According to the present invention, the antigen can be any molecule including, without limitation, proteins, peptides, polysaccharides, glycoproteins, glycolipids, nucleic acids, and any combination thereof. In a specific embodiment, the antigen is presented by a recombinant virus expressing said antigen. Preferably, the virus is selected from the group consisting of a recombinant adenovirus, recombinant pox virus, recombinant Sindbis virus, recombinant yellow fever virus, and recombinant dengue virus.

The antigens useful in the methods and compositions of the present invention include without limitation various viral, bacterial, fungal, parasite-specific, tumor-specific, and autoimmune disease-specific antigens. Non-limiting examples of viral antigens of the invention include antigens derived from influenza virus (e.g., surface glycoproteins hemagluttinin (HA) and neuramimidase (NA)); immunodeficiency virus (e.g., a human immunodeficiency virus antigens (HIV) such as gp120, gp160, p18 antigen Gag p17/p24, Tat, Pol, Nef, and Env); herpesvirus (e.g., a glycoprotein from herpes simplex virus (HSV), Marek's Disease Virus, cytomegalovirus (CMV), or Epstein-Barr virus); hepatitis virus (e.g., Hepatitis B surface antigen (HBsAg)); papilloma virus; rous associated virus (e.g., RAV-1 env); infectious bronchitis virus (e.g., matrix and/or preplomer); flavivirus (e.g., a Japanese encephalitis virus (JEV) antigen, a Yellow Fever antigen, or a Dengue virus antigen); Morbillivirus (e.g., a canine distemper virus antigen, a measles antigen, or rinderpest antigen such as HA or F); rabies (e.g., rabies glycoprotein G); parvovirus (e.g., a canine parvovirus antigen); poxvirus (e.g., an ectromelia antigen, a canary poxvirus antigen, or a fowl poxvirus antigen); chicken pox virus (varicella zoster antigen); infectious bursal disease virus (e.g., VP2, VP3, or VP4); Hantaan virus, and mumps virus. Non-limiting examples of bacterial antigens of the invention include lipopolysaccharides isolated from gram-negative bacterial cell walls and *staphylococcus*-specific, *streptococcus*-specific, pneumococcus-specific (e.g., PspA; see PCT Publication No. WO 92/14488), *Neisseria gonorrhea*-specific, *Borrelia*-specific (e.g., OspA, OspB, OspC antigens of *Borrelia* associated with Lyme disease such as *Borrelia burgdorferi*, *Borrelia afzelli*, and *Borrelia garinii* [see, e.g., U.S. Pat. No. 5,523,089; PCT Publication Nos. WO 90/04411, WO 91/09870, WO 93/04175, WO 96/06165, WO93/08306; PCT/US92/08697; Bergstrom et al., *Mol. Microbiol.*, 1999; 3: 479486; Johnson et al., *Infect. and Immun.* 1992; 60: 1845-1853; Johnson et al., *Vaccine* 1995; 13: 1086-1094; The Sixth International Conference on Lyme Borreliosis: Progress on the Development of Lyme Disease Vaccine, *Vaccine* 1995; 13: 133-135]), and pseudomonas-specific proteins or peptides. Non-limiting examples of malaria-specific antigens include irradiated plasmodial sporozoites and synthetic peptide antigens comprising at least one T-cell epitope of the malarial circumsporozoite (CS) protein. Non-limiting examples of fungal antigens include those isolated from candida (e.g., MP65 from *Candida albicans*), *trichophyton*, and ptyrosporum. Non-limiting examples of tumor-specific antigens include WT-1 antigen (in lymphoma and other solid tumors), ErbB receptors, Melan A [MART1], gp 100, tyrosinase, TRP-1/gp 75, and TRP-2 (in melanoma); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers) and such shared tumor-specific antigens as MAGE-2, MAGE-4, MAGE-6, MAGE-10, MAGE-12, BAGE-1, CAGE-1,2,8, CAGE-3 TO 7, LAGE-1, NY-ESO-1/LAGE-2, NA-88, GnTV, and TRP2-INT2. Non-limiting examples of autoimmune disease-specific antigens include GAD 65, IA-2 and insulin B chain (for type 1-diabetes), and myelin basic protein and glatiramer acetate (GA) (for multiple sclerosis).

In a specific embodiment, an antigen or an MHC molecule or both are encoded by an expression vector. In a preferred embodiment, the expression vector is an adenovirus vector, modified vaccinia Ankara vector, pVAX plasmid vector, pVR1012 plasmid vector, or pTHr plasmid vector. An antigen and an MHC molecule can be encoded by the same or different expression vectors. One construct expressing an MHC molecule and an antigen may more efficiently trigger an immune response as both proteins are made by the same cell. The expression of an antigen and an MHC molecule from the same expression vector can be controlled by one, two, or three promoters. The expression of an MHC molecule and an antigen under different promoters in the same construct can allow finer control over levels of expression of the MHC molecule and the antigen. The ratio between the level of an MHC molecule and the level of an antigen may be important for optimizing an antigen-specific T-cell response (see, e.g., Barouch et al., *Science* 2000; 290:486-92; Werle et al., *Vaccine* 1999; 17:2983-90). Non-limiting examples of promoters useful for expression of MHC molecules include EXV-3, CMV, HEF-1α, and Rous sarcoma virus (RSV) promoters. In one embodiment, the expression of an antigen and an MHC molecule from the same expression vector results in the production of a fusion protein comprising both the antigen and the MHC molecule. In another embodiment, the expression of an antigen and an MHC molecule from the same expression vector results in the production of two different proteins.

In a specific embodiment, the present invention discloses a method for augmenting an immune response to a sporozoite stage of malaria in a susceptible mammalian host comprising conjointly administering to said host: (i) at least one malaria-specific antigen in a first amount, and (ii) an allogenic or syngenic MHC molecule in a second amount, said first and second amounts being effective in combination to augment the immune response mounted against said antigen by the host, as compared to the immune response that the host could have mounted upon the administration of said first amount of said antigen without the conjoint administration of said MHC molecule. Thus, as disclosed in Example 1, infra, a co-administration to BALB/c mice (H-$2^d$ haplotype) of (i) a sub-optimal dose of a recombinant adenovirus expressing *P. yoelii* CS protein (AdPyCS) and (ii) syngenic BALB/c splenocytes (H-$2^d$ haplotype) or allogenic C57BL/6 (B6) splenocytes (H-$2^b$ haplotype) (but not xenogenic human peripheral blood lymphocytes (PBLs)) significantly enhances CS-specific CD4+ and CD8+ T cell responses. As further disclosed in Example 4, infra, intramuscular (i.m.) co-administration to BALB/c mice (H-$2^d$ haplotype) of (i) a sub-optimal dose of a recombinant adenovirus expressing *P. yoelii* CS protein (AdPyCS) and (ii) 3 µg of pVAX plasmid encoding the allogenic MHC molecule H-$2K^b$ (pVAX-H-$2K^b$) enhanced the number of CS-specific CD8+ T-cell responses approximately 2-fold, as compared to that elicited by AdPyCS immunization alone.

A preferred malaria-specific antigen according to the invention comprises irradiated plasmodial sporozoites or a synthetic peptide antigen comprising a T cell epitope of the malarial circumsporozoite (CS) protein such as CD4+ T cell epitope YNRNIVNR LLGDALNGKPEEK (SEQ ID NO: 1) or CD8+ T cell epitope SYVPSAEQI (SEQ ID NO: 2) of *P. yoelii* CS protein (Renia et al., *J. Immunol.* 1993; 22: 157-160; Rodrigues et al., *Int. Immunol.* 1991; 3: 579-585), or CD4+ T cell epitope (NVDPNANP)n (SEQ ID NO: 3), or CD4+/CD8+ T cell epitope EYLNKIQNSLSTEWSPCSVT (SEQ ID NO: 4) of *P. falciparum* CS protein (Nardin et al., *Science* 1989; 246:1603; Moreno et al., *Int. Immunol.* 1991; 3: 997; Moreno et al., *J. Immunol.* 1993; 151: 489), or an epitope derived from, and reactive with, other malarial components, such as, for example, the *P. vivax* Erythrocyte Secreted Protein-1 or -2 (PvESP-1 or PvESP-2) (see, e.g., U.S. Pat. No. 5,874,527), *P. falciparum* sporozoite surface protein designated Thrombospondin Related Adhesion (Anonymous) protein (TRAP), also called Sporozoite Surface Protein 2 (SSP2), LSA I, hsp70, SALSA, STARP, Hep17, MSA, RAP-1, and RAP-2. In one embodiment, epitope components are incorporated into a fusion protein. In another embodiment, epitope components are incorporated into multiple antigen peptides (MAPs), forming a synthetic macromolecular polypeptide containing a high density of the epitopes. Methods for MAP synthesis are well known in the art (see, e.g., Tam, *Proc. Natl. Acad. Sci. USA* 1988; 85: 5409; Tam, *Meth. Enzymol.* 1989; 168: 7). The present invention also encompasses T-cell epitopes derived from other plasmodial species, including without limitation *P. malariae, P. ovale, P. reichenowi, P. knowlesi, P. cynomolgi, P. brasilianum, P. berghei,* and *P. chabaudi*. These epitopes typically comprise between 8 and 18 amino acid residues, derived from a plasmodial protein.

In another specific embodiment, the present invention provides a method for augmenting an immune response to an HIV antigen in a susceptible mammalian host comprising conjointly administering to said host: (i) at least one HIV-specific antigen in a first amount, and (ii) an allogenic or syngenic MHC molecule in a second amount, said first and second amounts being effective in combination to augment the immune response mounted against said antigen by the host, as compared to the immune response that the host could have mounted upon the administration of said first amount of said antigen without the conjoint administration of said MHC molecule. Thus, as disclosed in Example 3, infra, intramuscular (i.m.) co-administration to BALB/c mice (H-$2^d$ haplotype) of (i) a sub-optimal dose of pVAX plasmid encoding HIV-Gag (ADVAX1) and (ii) 3 µg of pVAX plasmid encoding the allogenic MHC molecule H-$2K^b$ (pVAX-H-$2K^b$) enhanced the number of Gag-specific CD8+ T-cell responses approximately 20-fold, as compared to that elicited by ADVAX1 immunization alone.

A preferred HIV-specific antigen according to the invention comprises a T cell epitope of Gag, Tat, Pol, Env, Nef, gp160, p8, and gp120. Non-limiting examples of HIV-specific antigens useful in the methods of the present invention include CD8+ T cell epitope RGPGRAFVTI (SEQ ID NO: 5) of p18 protein, or Gag p24 CD8+ T cell epitopes (e.g., KAFSPEVIPMF (aa 30-40, SEQ ID NO: 6), KAFSPEVI (aa 30-37, SEQ ID NO: 7), TPQDLNM (or T) ML (aa 180-188, SEQ ID NOS: 8 and 9), DTINEEAAEW (aa 203-212, SEQ ID NO: 10), KRWIILGLNK (aa 263-272, SEQ ID NO: 11), and QATQEVKNW (aa 308-316, SEQ ID NO: 12)), or Gag p17 CD8+ T cell epitopes (e.g., RLRPGGKKK (aa 20-29, SEQ ID NO: 13) and SLYNTVATL (aa 77-85, SEQ ID NO: 14)) (see, e.g., Goulder et al., *J. Virol.* 2000; 74:5291-9; Cao et al., *J. Immunol.* 2003; 171:3837-46; Kelleher et al., *J Exp Med.* 2001; 193:375-86; Goulder et al., *J Exp Med.* 1997; 185:1423-33; Kaul et al., *Immunol Lett.* 2001; 79:3-13; Gahery-Segard et al., *J. Virol.* 2003; 77:11220-31).

In yet another specific embodiment, the present invention provides a method for augmenting an immune response to a cancer-associated/tumor-specific antigen in a susceptible mammalian host comprising conjointly administering to said host: at least one cancer-associated/tumor-specific antigen in a first amount, and an allogenic or syngenic MHC molecule in a second amount; said first and second amounts being effective in combination to augment the immune response mounted against said antigen by the host compared to the immune response that the host could have mounted upon the administration of said first amount of said antigen without the conjoint administration of said MHC molecule. Non-limiting examples of cancer-associated/tumor-specific antigens include ErbB receptors, Melan A [MART1], gp100, tyrosinase, TRP-1/gp 75, and TRP-2 (in melanoma; for additional examples, see also a list of antigens provided in Storkus and Zarour, Forum (Genova), 2000 Jul.-Sep., 10(3):256-270); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers), P1A tumor antigen (e.g., CTL epitope LPYLGWLVF [SEQ ID NO: 15] as disclosed in WO 98/56919), and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2-INT2 a chimeric tumor CTL epitope string such as MLPYLGWLVF-AQHPNAELL-KHYLFRNL-SPSYVYHQF-IPNPLLGLD (SEQ ID NO: 16) (see, e.g., PCT Application No. WO 98/56919).

In yet another specific embodiment, the present invention provides a method for augmenting an immune response to an autoimmune disease antigen in a susceptible mammalian host comprising conjointly administering to said host: at least one antigen in a first amount, and an allogenic or syngenic MHC molecule in a second amount; said first and second amounts being effective in combination to augment the immune response mounted against said antigen by the host compared to the immune response that the host could have mounted upon the administration of said first amount of said antigen without the conjoint administration of said MHC molecule. Non-limiting examples of autoimmune disease-associated antigens include GAD 65, IA-2 and insulin B chain (for type 1-diabetes), and myelin basic protein and glatiramer acetate (GA) (for multiple sclerosis).

As the adjuvants comprising allogenic or syngenic MHC molecules exert their immunostimulatory activity in combination with a plurality of different antigens, they are therefore useful for both preventive and therapeutic applications. Accordingly, in a further aspect, the invention provides a prophylactic and/or therapeutic method for treating and/or preventing a disease in a mammal comprising conjointly administering to said mammal: (i) an antigen associated with the disease in a first amount, and (ii) an allogenic or syngenic MHC molecule in a second amount, said first and second amounts being immunogenically effective in combination. As specified herein, this method can be useful for preventing and/or treating various infectious, neoplastic and autoimmune diseases including allergies.

Non-limiting examples of infectious diseases that can be treated using the method of the invention include viral infections (such as those caused by influenza viruses, leukemia viruses, autoimmune diseases caused by immunodeficiency viruses such as HIV, papilloma viruses, herpes virus, hepatitis viruses, measles virus, poxviruses, mumps virus, cytomegalovirus [CMV], Epstein-Barr virus, etc.), bacterial infections (such as those caused by *staphylococcus, streptococcus*, pneumococcus, *Neisseria gonorrhea, Borrelia*, pseudomonas, etc.), parasitic infections (such as those caused by plasmodial species, etc.), and fungal infections (such as those caused by candida, trichophyton, ptyrosporum, etc.).

Non-limiting examples of neoplastic and cell proliferative diseases and disorders that can be treated using the method of the invention include blood cancers (such as hematopoietic tumors of lymphoid lineage, including leukemia, acute lymphocitic leukemia, acute lymphoblastic leukemia, B cell lymphoma, T cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia) or solid tumors such as carcinomas (e.g., bladder, breast, colon, kidney, liver, lung, including small cell lung cancer, non-small cell lung cancer, esophagus, gall bladder, ovary, pancreas, testicular, stomach, renal, liver, cervix, thyroid, prostate, and skin, including squamous cell carcinoma), tumors of mesenchymal origin (including fibrosarcoma and rhabdomyosarcoma), tumors of the central and peripheral nervous system (including astrocytoma, neuroblastoma, glioma and schwannomas), melanoma, seminoma, teratocarcinoma, osteosarcoma, xenoderoma pigmentosum, keratoctanthoma, thyroid follicular cancer and Kaposi's sarcoma, benign prostate hyperplasia, familial adenomatosis polyposis, neuro fibromatosis, psoriasis, vascular smooth cell proliferation associated with atherosclerosis, pulmonary fibrosis, arthritis glomerulonephritis and post-surgical stenosis and restenosis.

Non-limiting examples of automimune diseases that can be treated using the method of the invention include rheumatoid arthritis, insulin-dependent diabetes mellitus, autoimmune thyroiditis, multiple sclerosis, uveoretinitis, lupus erythematosus, scleroderma, psoriatic arthritis, myasthenia gravis, juvenile onset diabetes, glomerulonephritis, Behcet's disease, Crohn's disease, ulcerative colitis, bullous pemphigoid, sarcoidosis, psoriasis, ichthyosis, Graves opththalmopathy, allergy, and asthma.

The methods of the invention can be used in conjunction with other treatments. For example, an anti-cancer treatment using tumor-specific antigen and allogenic or syngenic MHC-based adjuvant of the present invention can be used in combination with chemotherapy and/or radiotherapy and/or IL-12 treatment. Anti-viral vaccines comprising allogenic or syngenic MHC-based adjuvant can be used in combination with IFN-α treatment. Vaccines against autoimmune diseases comprising allogenic or syngenic MHC-based adjuvant can be used in combination with, for example, GAD 65, IA-2 or insulin B chain (for type 1-diabetes), and myelin basic protein or glatiramer acetate (GA) (for multiple sclerosis).

In addition to their therapeutic or prophylactic applications, the allogenic or syngenic MHC molecules of the invention can be used as a research tool to study various aspects of basic immunology. For example, allogenic or syngenic MHC molecules of the invention can be used to study immune mechanisms such as antigen presentation by antigen presenting cells (APC), and modulation of immune responses by cytokines and their receptors. Such allogenic or syngenic MHC molecules can be also employed in vaccine design research. When used with different MHC molecules, the same antigen may produce immune responses of varying intensity and/or length.

6.5. Pharmaceutical and Vaccine Compositions of the Invention

In conjunction with the methods of the present invention, also provided are immunogenic compositions comprising an immunogenically effective amount of (i) an antigen and (ii) an allogenic or syngenic MHC molecule as well as, optionally, an additional carrier (preferably pharmaceutically acceptable).

The antigens used in immunogenic (e.g., vaccine) compositions of the instant invention can be derived from a eukaryotic cell (e.g., tumor, parasite, fungus), bacterial cell, viral particle, or any portion thereof. In the event the material to which the immunogenic response is to be directed is poorly antigenic, it may be additionally conjugated to a carrier molecule such as albumin or hapten, using standard covalent binding techniques, for example, with one of the several commercially available reagent kits.

Examples of specific antigens and MHC molecules useful in the compositions of the present invention are provided in Section 6.4., supra.

The foregoing list of antigens are intended as exemplary, as the antigen of interest can be derived from any animal or human pathogen or tumor. With respect to DNA encoding pathogen-derived antigens of interest, attention is directed to, e.g., U.S. Pat. Nos. 4,722,848; 5,174,993; 5,338,683; 5,494,807; 5,503,834; 5,505,941; 5,514,375; 5,529,780; U.K. Patent No. GB 2 269 820 B; and PCT Publication Nos. WO 92/22641; WO 93/03145; WO 94/16716; WO 96/3941; PCT/US94/06652. With respect to antigens derived from tumor viruses, reference is also made to Molecular Biology of Tumor Viruses, RNA Tumor Viruses, Second Edition, Edited by Weiss et al., Cold Spring Harbor Laboratory Press, 1982. For a list of additional antigens useful in the compositions of the invention see also Stedman's Medical Dictionary (24th edition, 1982).

To provide additional antigen-derived T-cell epitopes for use in the compositions of the present invention, these epitopes may be identified by one or a combination of several methods well known in the art, such as, for example, by (i) fragmenting the antigen of interest into overlapping peptides using proteolytic enzymes, followed by testing the ability of individual peptides to induce T-cell actuation (see, e.g., Janis Kuby, *Immunology*, pp. 79-80, W.H. Freeman, 1992); (ii) preparing synthetic peptides whose sequences are segments or analogs of a given antigen (see, e.g., Alexander et al., *Immunity* 1994; 1:751-61; Hammer et al., *J. Exp. Med.* 1994; 180:2353-8), or constructs based on such segments, or analogs linked or fused to a carrier or a heterologous antigen and testing the ability of such synthetic peptides to elicit T-cell activation (e.g., testing their ability to interact with MHC class II molecules both in vitro and in vivo [see, e.g., O'Sullivan et al., *J. Immunol.* 1991; 147:2663-9; Hill et al., *J. Immunol.* 1991; 147:189-197]); for determination of T-cell epitopes, peptides should be at least 8 to 10 amino acids long to occupy the groove of the MHC class I molecule and at least 13 to 25 amino acids long to occupy the groove of MHC class II molecule, preferably, the peptides should be longer; these peptides should also contain an appropriate anchor motif which will enable them to bind to various class I or class II MHC molecules with high enough affinity and specificity to generate an immune response (see Bocchia et al., *Blood* 1995; 85: 2680-2684; Englehard, *Ann. Rev. Immunol.* 1994; 12: 181); (iii) sequencing peptides associated with purified MHC molecules (see, e.g., Nelson et al., *Proc. Natl. Acad. Sci. USA*, 1997; 94:628-33); (iv) screening a peptide display library for high-affinity binding to MHC class II molecules, TCR, etc. (see, e.g., Hammer et al., *J. Exp. Med.* 1992; 176:1007-13); (v) computationally analyzing different protein sequences to identify, e.g., hydrophilic stretches (hydrophilic amino acid residues are often located on the surface of the protein and are therefore accessible to the antibodies) and/or high-affinity TCR or MHC class II allele-specific motifs, e.g., by comparing the sequence of the protein of interest with published structures of peptides associated with the MHC molecules (Mallios, *Bioinformatics* 1999; 15:432-439; Milik et al., *Nat. Biotechnol.* 1998; 16:753-756; Brusic et al., *Nuc. Acids Res* 1998; 26:368-371; Feller and de la Cruz, *Nature*, 1991; 349: 720-721); (vii) generating monoclonal antibodies to various portions of the antigen of interest, and then ascertaining whether those antibodies attenuate in vitro or in vivo growth of the pathogen or tumor from which the antigen was derived (see U.S. Pat. No. 5,019,384 and references cited therein).

In a specific embodiment, the antigen of the invention may be presented by a recombinant virus expressing said antigen. Preferably, the virus is selected from the group consisting of a recombinant adenovirus, recombinant pox virus, recombinant Sindbis virus, recombinant yellow fever virus, and recombinant dengue virus.

Preferably, in the disclosed compositions, both the antigen and the allogenic or syngenic MHC molecule are present in immunogenically effective amounts. For each specific antigen, the optimal immunogenically effective amount should be determined experimentally (taking into consideration specific characteristics of a given subject and/or type of treatment). Generally, this amount is in the range of 0.01 mg-1.0 mg of an antigen per kg of the body weight. For adjuvant of the present invention, allogenic or syngenic MHC molecule, the optimal immunogenically effective amount is preferably in the range of 0.01 mg-0.1 mg per kg of the body weight.

The MHC-based adjuvant of the invention can be administered as part of a pharmaceutical or vaccine composition comprising an antigen or as a separate formulation, which is administered conjointly with a second composition containing an antigen. In any of these compositions the MHC molecule can be combined with other adjuvants and/or carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues (e.g., N-acetyl-muramyl-L-threonyl-D-isoglutanine [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, or synthetic polynucleotides, and surface active substances such as lysolecithin, pluronic polyols, polyanions, peptides, hydrocarbon emulsions, or keyhole limpet hemocyanins (KLH). Preferably, these additional adjuvants are also pharmaceutically acceptable for use in humans.

The invention also provides a method for preparing an immunogenic composition. comprising at least one antigen and an allogenic or syngenic MHC molecule, said method comprising admixing the MHC molecule and the antigen, and optionally one or more pharmaceutically acceptable carriers. The invention also provides a method for preparing an immunogenic composition comprising an expression vector encoding at least one antigen and an allogenic or syngenic MHC molecule, said method comprising admixing the expression vector with one or more pharmaceutically acceptable carriers. Further, the invention provides a method for preparing an immunogenic composition comprising a first expression vector encoding at least one antigen and a second expression vector encoding an allogenic or syngenic MHC molecule, said method comprising admixing the first expression vector with the second expression vector any optionally with one or more pharmaceutically acceptable carriers.

6.6. Formulations and Administration

The invention provides pharmaceutical and immunogenic formulations containing (one or more antigens and allogenic or syngenic MHC molecules either as a single composition or as two separate compositions which can be administered simultaneously or sequentially), which formulations are suitable for administration to elicit an antigen-specific immune response for the treatment and prevention of infectious, neoplastic or autoimmune diseases. Compositions of the present invention can be formulated in any conventional manner using one or more pharmaceutically acceptable carriers.

Preferably, the immunogenic formulations of the invention are delivered by subcutaneous (s.c.), intramuscular (i.m.), intradermal (i.d.), intranasal, or oral administration. Formulations for injection can be presented in unit dosage form, e.g., in ampoules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

As disclosed herein, an antigen and allogenic or syngenic MHC molecules can be mixed with pharmaceutically acceptable carriers. Suitable carriers are, for example, water, saline, buffered saline, dextrose, glycerol, ethanol, sterile isotonic aqueous buffer or the like and combinations thereof. In addition, if desired, the preparations may also include minor amounts of auxiliary substances such as wetting or emulsifying agents, pH buffering agents, and/or immune stimulators (e.g., adjuvants in addition to allogenic or syngenic MHC molecules) that enhance the effectiveness of the pharmaceutical composition or vaccine. Non-limiting examples of additional immune stimulators which may enhance the effectiveness of the compositions of the present invention include immunostimulatory, immunopotentiating, or pro-inflammatory cytokines, lymphokines, or chemokines or nucleic acids encoding them (specific examples include interleukin (IL)-1, IL-2, IL-3, IL-4, IL-12, IL-13, granulocyte-macrophage (GM)-colony stimulating factor (CSF) and other colony stimulating factors, macrophage inflammatory factor, Flt3 ligand. These additional immunostimulatory molecules can be delivered systemically or locally as proteins or by expression of a vector that codes for expression of the molecule. The techniques described above for delivery of the antigen and allogenic or syngenic MHC molecule can also be employed for the delivery of additional immunostimulatory molecules.

The invention also provides a pharmaceutical pack or kit comprising one or more containers filled with one or more of the ingredients of the immunogenic formulations of the invention. In a related embodiment, the present invention provides a kit for the preparation of a immunogenic composition comprising at least one antigen and an allogenic or syngenic MHC molecule, and optionally instructions for admixing the antigen and the MHC molecule and/or for administration of the composition. The kit may also optionally include one or more physiologically acceptable carriers and/or auxiliary substances. Associated with the kit can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient (i.e., an antigen and/or an allogenic or syngenic MHC molecule). The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

6.7. Effective Dose and Safety Evaluations

According to the methods of the present invention, the pharmaceutical and immunogenic compositions described herein are administered to a patient at immunogenically effective doses, preferably, with minimal toxicity.

Following methodologies which are well-established in the art (see, e.g., reports on evaluation of several vaccine formulations containing novel adjuvants in a collaborative effort between the Center for Biological Evaluation and Food and Drug Administration and the National Institute of Allergy and Infectious Diseases [Goldenthal et al., National Cooperative Vaccine Development Working Group. AIDS Res. Hum. Retroviruses 1993, 9:545-9]), effective doses and toxicity of the compounds and compositions of the instant invention are first determined in preclinical studies using small animal models (e.g., mice) in which both the antigen and allogenic or syngenic MHC molecule have been found to be immunogenic and that can be reproducibly immunized by the same route proposed for the human clinical trials. Specifically, for any pharmaceutical composition or vaccine used in the methods of the invention, the therapeutically effective dose can be estimated initially from animal models to achieve a circulating plasma concentration range that includes the IC50 (i.e., the concentration of the test compound which achieves a half-maximal inhibition of symptoms). Dose-response curves derived from animal systems are then used to determine testing doses for the initial clinical studies in humans. In safety determinations for each composition, the dose and frequency of immunization should meet or exceed those anticipated for use in the clinical trial.

As disclosed herein, the dose of antigen and allogenic or syngenic MHC molecule, and other components in the compositions of the present invention is determined to ensure that the dose administered continuously or intermittently will not exceed a certain amount in consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices and should be decided according to the judgment of the practitioner and each patient's circumstances according to standard clinical techniques. In this connection, the dose of an antigen is generally in the range of 0.01 mg-1.0 mg per kg of the body weight, and the dose of the allogenic or syngenic MHC molecule required for augmenting the immune response to the antigen is generally in the range of 0.01 mg-0.1 mg per kg of the body weight.

Toxicity and therapeutic efficacy of allogenic or syngenic MHC molecule(s) in immunogenic compositions of the invention can be determined by standard pharmaceutical procedures in experimental animals, e.g., by determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. While therapeutics that exhibit toxic side effects can be used (e.g., when treating severe forms of cancer, life-threatening infections or autoimmune diseases), care should be taken to design a delivery system that targets such immunogenic compositions to the specific site in order to minimize potential damage to other tissues and organs and, thereby, reduce side effects. In this respect, the advantage of the present invention is that, to exert the most potent effect, an antigen and MHC-based adjuvant are administered locally. As disclosed herein, the adjuvant of the invention is not only highly immunostimulating at relatively low doses (e.g., 10-100 μg of the adjuvant per kg of the body weight) but also possesses low toxicity and does not produce significant side effects.

As specified above, the data obtained from the animal studies can be used in formulating a range of dosage for use in humans. The therapeutically effective dosage of allogenic or syngenic MHC molecules of the present invention for use in humans lies preferably within a range of circulating concentrations that include the ED50 with little or no toxicity. The dosage can vary within this range depending upon the dosage form employed and the route of administration utilized. Ideally, a single dose should be used.

7. EXAMPLES

The following Examples illustrate the invention without limiting its scope.

7.8. Example 1

Cells Carrying Allogenic and Syngenic MHC Molecules Enhance Antigen-specific T cell Immune Responses

7.8.1. Methods

Splenocyte isolation. After removing the spleen, splenocytes are obtained by gently teasing the spleen by grinding it between two autoclaved microscopic slides in a Petri dish containing 5 ml of DMEM containing 10% FCS. This cell suspension is passed through a nylon mesh, and washed three times with the medium. The pellet is resuspended in culture medium, which consists of DMEM medium supplemented with 10% FCS.

Human Peripheral Blood Lymphocyte (PBL) isolation. Blood was obtained from both healthy volunteers and Multiple Sclerosis (MS) patients collected in standard citrate-phosphate-dextrose unit bags or in 3-4 15-ml heparinized Vacutainer™ tubes (Becton Dickinson #6489, San Jose, Calif.) and used within 24 h of collection. PBL were purified by density centrifugation (450×g for 30 min) on Ficoll (Pharmacia LKB, Uppsala, Sweden), isolated from the gradient interface, washed twice in Dulbecco's phosphate buffered saline (DPBS, BioWhittaker #17-512Q, Walkersville, Md.), and resuspended in DME medium supplemented with 10% FCS.

Modes of administration. Mice were administered s.c. (50 μl each at both thighs) with a single dose of indicated amounts of cells or DNA, at the time of immunization with a recombinant adenovirus expressing *P. yoelii* CS protein.

Immunization with recombinant viruses and DNA plasmids. A sub-optimal dose (1×10⁷ p.f.u.) of recombinant adenovirus expressing the entire *P. yoelii* CS protein, AdPyCS (Rodrigues et al., *J. Immunol.*, 158: 1268-1274, 1997), was used to immunize mice.

Mice. BALB/c (H-$2^d$ haplotype) and C57BL/6 (B6) mice (H-$2^b$ haplotype) were purchased from The Jackson Laboratory (Bar Harbor, Me.) and maintained under the pathogen-free condition in the Animal Facility of the Department of Medical and Molecular Parasitology at New York University School of Medicine. Mice of either sex were used at 6-8 weeks. Groups of BALB/c (H-$2^d$ haplotype) mice (3 or 4 per group) were co-administered s.c. a sub-optimal dose (1×10⁶ p.f.u.) of AdPyCS and 6×10⁵ splenocytes from BALB/c mice (H-$2^d$ haplotype), C57BL/6 (B6) mice (H-$2^b$ haplotype), or human PBL. Mice immunized with AdPyCS alone were used as a control.

Quantification of epitope-specific CD4+ and CD8+ T-cells by an ELISPOT assay. Two weeks after immunization, unfractionated splenocytes from BALB/c mice (H-$2^d$ haplotype) immunized with AdPyCS and splenocytes from BALB/c mice or B6 mice or PBL or control mice (immunized only with AdPyCS) were assayed to determine the number of CS-specific CD4⁺ and CD8⁺ T-cells producing IFN-gamma using ELISPOT assay (Miyahira et al, *J. Immunol. Methods* 1995; 181: 45-54). Briefly, 96-well nitrocellulose plates (Millipone, Bedford, Mass.) were coated overnight at room temperature with biotinylated anti-mouse IFN-gamma monoclonal antibodies (mAb). After several washes with PBS, serial dilution of splenocytes from 5×10⁵ cells/200 μl down to 500 cells/200 μl in culture medium in the presence or absence of 10 μg/ml of peptides corresponding to CD8+ or CD4+ epitope were incubated for 20-24 hours at 37° C. in a 5% $CO_2$ incubator in plates coated with anti-mouse IFN-gamma mAb, R4. Following incubation, the plates were washed fives times with PBS-T. Plates were then incubated for 3 hours at room temperature with biotinylated anti-mouse IFN-γ mAb (XMG-1.2) in the plates. The plates were washed four times with PBS-T before the addition of Streptavidin-AP conjugate and the incubation for 1 hour at room temperature. Following an additional four washes with PBS-T and one wash with distilled water, spots were developed with one step BCIP/NPT reagent. Spots were counted using Immune Spot Reader (Cellular Technology Ltd., Cleveland, Ohio).

Statistical analysis. Student's t test was used for all comparisons. Only P values below 0.01 were considered significant. Data are presented as mean values±SD.

7.8.2. Results and Discussion

To test the hypothesis whether a highly acute and vigorous allo-reactive and auto-reactive T cell responses can enhance the immunogenicity of vaccines, the adjuvant effects of lymphocytes obtained from syngenic or allogenic mice, and from xenogeneic human cells were tested. As shown in FIG. 1, subcutaneous (s.c.) co-administration to BALB/c mice (H-$2^d$ haplotype) of (i) a sub-optimal dose (1×10⁶ p.f.u.) of a recombinant adenovirus expressing *P. yoelii* CS protein (AdPyCS) and (ii) 6×10⁵ allogenic C57BL/6 (B6) splenocytes (H-$2^b$ haplotype) significantly enhanced (3-fold) the level of CS-specific CD4+ and CD8+ T cell responses, as compared to mice immunized with AdPyCS alone. Surprisingly, syngenic splenocytes (H-$2^d$ haplotype) derived from BALB/c mice also enhanced the level of CS-specific CD4+ and CD8+ T cell responses 2-fold. This suggests that not only allo-reactive cells, but also auto-reactive cells are able to contribute to the enhancement of acquired immune response. Xenogenic lymphocytes (human PBL) not only failed to increase CS-specific responses, but rather suppressed the responses.

7.9. Example 2

Subcutaneous Co-administration of an Antigen and Allogenic Splenocytes Induces a More Effective Immune Response than Intravenous Co-administration

7.9.1. Methods

Splenocyte isolation, mice manipulations, ELISPOT assay, and Statistical analysis were performed as described as in Example 1, supra.

Modes of Administration. BALB/c mice (H-$2^d$ haplotype) were administered subsutaneously (s.c.) (50 μl each at both sides of the base tail) with a single dose (6×10⁵) of allogenic C57BL/6 (B6) splenocytes (H-$2^b$ haplotype).

Parasites and their use for immunization and challenge. *P. yoelii* (17×NL strain) sporozoites were obtained by dissecting the mosquito salivary glands as described (Rodrigues et at, *Int. Immunol.*, 3: 579-585, 1991; Gonzalez-Aseguinolaza et al., *Proc. Natl. Acad. Sci. USA*, 97: 8461-8466, 2000). For immunization, a sub-optimal dose (1×10⁴) of sporozoites were radiation-attenuated by exposing them to 12,000 rad, and then injected i.v. into the tail vein or s.c. into both sides of the base tail of the mice. 1×10⁴ irradiated sporozoites were used to immunize mice. Quantification of CD4+ and CD8+ T cells was performed using ELISPOT assay.

7.9.2. Results and Discussion

Irradiated *P. yoelii* sporozoites were used as an antigen to test the effect of route of administration on the adjuvant effect of allogenic C57BL/6 (B6) (H-$2^b$ haplotype) splenocytes. 6×10⁵ B6-derived splenocytes were administered subcutaneously (s.c.) to BALB/c mice (H-$2^d$ haplotype) with a sub-optimal dose (1×10⁴) of irradiated *P. yoelii* sporozoites either subcutaneously (s.c.) or intravenously (i.v.). As shown in FIG. 2, co-administration of sporozoites and B6 splenocytes by a subcutaneous route induced a 3-4 fold higher level of CS-specific CD4+ and CD8+ T-cell responses than those elicited by sporozoite immunization alone. In contrast, when irradiated sporozoites and B6 splenocytes were administered by intravenous route and subcutaneous route, respectively, there was no significant enhancement of CS-specific T-cell responses compared to those elicited by sporozoite immunization alone. It follows that s.c. immunization conjointly results in a much stronger adjuvant effect of allo-MHC than administering immunogen and allo-MHC through different routes.

7.10. Example 3

Co-Administration of a Plasmid Encoding HIV-Gag and a Plasmid Encoding the Allogenic MHC Molecule H-$2K^b$ Significantly Potentiates Gag-Specific CD8+ T Cell Responses

7.10.1. Methods

Mice manipulations, ELISPOT assay, and statistical analysis were performed as described in Example 1, supra.

Immunization with recombinant DNA plasmids. A sub-optimal dose (15 μg) of a naked DNA plasmid pVAX (Invitrogen V260-20) encoding an HIV-Gag sequence (ADVAX1), was used to immunize mice.

ADVAX1 (pEnv/Gag) vaccine is based on pVAX1, a commercially-available plasmid from Invitrogen® (Catalogue No. V260-20) (FIG. 3). This vector was designed specifically for use in the development of DNA vaccines, and was constructed to be consistent with United States Food and Drug Administration (FDA) guidelines. The original vector was modified by inserting an additional promoter. PCR was used to amplify the human elongation factor 1α (hEF1α) promoter from pBudCE4.1, a commercially-available vector (Invitrogen®, Catalogue No. V532-20). The promoter was then cloned into the EcoR1/Not1 sites of pVAX1 and the new construction was verified with sequencing. The hEF1α promoter has been well-characterized by others. This alteration of pVAX1, yielding pADVAX (FIG. 4), permits independent, high-level expression of a second genetic insert.

Of note, the bicistronic capacity of pADVAX is more potent (by 10- to 20-fold) than that achieved with use of an internal ribosomal entry site, or IRES. By western blot, it can be seen that the level of protein expression from each gene under the dual promoters of pADVAX is comparable to that driven by the CMV promoter alone in pVAX1.

After constructing the vector, viral genes for insertion were prepared. ADVAX1 vaccine was to contain HIV-1 env and gag, but first the inventors synthesized the genes anew, so that they included codons that are optimal for mammalian expression. So-called "codon optimization" apparently represents a facilitation of Rev/RRE-independent nuclear export, and is consistently found to enhance expression of viral genes. Overlapping PCR was used to unite oligonucleotides (80- to 90-mers overlapping by 16-18) with sequences reflecting this ideal codon selection. In doing so, gene expression was enhanced by 100- to 1000-fold.

The genes were then further modified by incorporating a tissue plasminogen activator (tPA) leader sequence MDAMKRGLCCVLLLCGAVFVSAR (SEQ ID NO: 17), replacing the native sequence of env and supplementing the gag gene. Of note, this sequence is thought to enhance expression in part by facilitating transport of protein from the endoplasmic reticulum (ER) to the Golgi apparatus.

The optimized HIV env nucleotide sequence, including the tPA leader sequence, is set forth as SEQ ID NO: 18. The optimized HIV gag nucleotide sequence, including the tPA leader sequence, is set froth as SEQ ID NO: 19. The amino acid sequence of Gag is set forth as SEQ ID NO: 20. The wild-type nucleotide sequence of gag is set forth as SEQ ID NO: 21 and the wild-type nucleotide sequence of env is set forth as SEQ ID NO: 22. With this refinement, gene expression was additionally enhanced by 5- to 10-fold. The final vaccine construct is schematically presented in FIG. 5.

The complete sequence of cDNA of H-2K$^b$ was identified in the NCBI database, (GenBank Accession Number U47328). This cDNA was cloned into EcoR1 site of pVAX1 plasmid (from Invitrogen as described above). After the ligation and the transformation, the recombinant plasmid containing H-2K$^b$, was identified. After a sequencing verification using corresponding primers, pVAX-H-2K$^b$ was transfected into 293 cells and the expression of H-2K$^b$ protein was confirmed using anti-Kb antibody.

Intramuscular injection. Different doses, ranging from 3 μg to 100 μg, of purified pVAX-H-2K$^b$ were divided into two and injected at both thigh of the mouse in a volume of 50 μl each.

Endotoxin testing. PyroGene™ Recombinant Factor C Assay (Cambrex Corporation, One Meadowlands Plaza, East Rutherford, N.J. 07073) was used to determine endotoxin concentration. A 96-well plate assay format was used to perform the PyroGene™ endotoxin assay. 100 μl of blank, endotoxin standards, and samples were added to appropriate wells of the microplate. To spike the samples with endotoxin, 10 μl of the 1 EU/ml solution was added to the appropriate wells. The plate was then pre-incubated in the reader at 37° C. for a minimum of 10 minutes. During the incubation period, the working reagent was prepared by mixing the rFC enzyme solution, assay buffer and substrate in a 1:4:5 ratio, respectively. 100 μl of the working reagent was dispensed to each well. Fluorescence at time zero was determined. The reaction was incubated for one hour and florescence at one hour was determined. The difference of time one-hour and time zero readings (ΔRFU) were corrected with the blank. The log net ΔRFU was then plotted against log endotoxin concentration in a linear regression curve and endotoxin concentration of samples was calculated according to the standard curve.

7.10.2. Results and Discussion

A plasmid encoding a murine allo-MHC molecule (pVAX-H-2K$^b$) was constructed for the purpose of adjuvant development based on the vector pVAX1. It was determined that pVAX-H-2K$^b$ is free (less than 0.01%) of endotoxin, which is known to have an independent adjuvant activity.

To test for pVAX-H-2K$^b$ adjuvant activity, BALB/c mice (H-2K$^d$ haplotype) were co-administered intramuscularly (i.m.) with different doses, ranging from 3 μg to 100 μg, of allogenic pVAX-H-2K$^b$ and a sub-optimal dose (15 μg) of pVAX plasmid encoding HIV-Gag (ADVAX1). HIV-Gag was selected because HIV-Gag-specific CD8+ T-cell responses were shown to associate with resistance to HIV seen among the prostitutes in Kenya (Rowland-Jones et al., *J Clin Invest.* 102:1758-65, 1998; Nabel, *Vaccine* 20:1945-7, 2002). As shown in FIG. 6, co-administration of 3 μg of pVAX-H-2K$^b$ enhanced the number of HIV-Gag-specific CD8+ T-cell responses approximately 20-fold, as compared to that elicited by ADVAX1 immunization alone. This indicates that an expression vector encoding an allo-MHC molecule can act as a potent adjuvant capable of strongly enhancing antigen-specific (e.g., HIV-specific) CD8+ T cell responses.

7.11. Example 4

Co-Administration of a Recombinant Adenovirus Expressing Malarial CS Protein and a Plasmid Encoding the Allogenic MHC Molecule H-2K$^b$ Potentiates CS-Specific CD8+ T Cell Responses 7.11.1. Methods Mice manipulations, ELISPOT assay, and statistical analysis were performed as described in Example 1, supra.

7.11.2. Results and Discussion

The adjuvant activity of allogenic pVAX-H-2K$^b$ on the immunogenicity of a recombinant adenovirus expressing *P. yoelii* CS protein (AdPyCS) was also tested. Different doses of pVAX-H-2K$^b$ ranging from 3 μg to 100 μg were co-administered with and a sub-optimal dose ($1 \times 10^6$ p.f.u.) of AdPyCS intramuscularly. Two weeks later, the number of CS-specific CD8+ T-cells was determined by an ELISPOT assay. As shown in FIG. 7, co-administration of 3 μg of pVAX-H-2K$^b$ increased the number of CS-specific CD8+ T cells two-fold. The lower level of pVAX-H-2K$^b$-mediated enhancement of CD8+ T cell responses with malaria-specific antigen AdPyCS versus HIV-specific antigen ADVAX1 may be attributable to the different vectors that were used for antigen expression.

This suggests that the use of the same type of vector for both antigen and MHC-based adjuvant might be important.

7.12. Example 5

Determination of Protective Anti-Malaria Immunity Induced by Co-Immunization of AdPvCS and Allogenic pVAX-H-2K$^b$

7.12.1. Methods

Mice manipulations, plasmid construction, route of administration, and isolation of sporozoites are as described in Examples 1, 2, and 3, supra.

Immunization and challenge. To determine the adjuvant effects of allo-MHC antigens on protection against malaria, H-2d mice, such as BALB/c (H-2$^d$ haplotype), are immunized with a suboptimal dose ($1 \times 10^6$ p.f.u.) of a recombinant adenovirus expressing *P. yoelii* CS protein (AdPyCS) in the presence of different amounts of pVAX plasmid encoding the allogenic MHC molecule H-2K$^b$ (pVAX-H-2K$^b$) ranging from 3 µg to 100 µg. AdPyCS-immunized mice receiving no pVAX-H-2K$^b$ are used as a control. To determine the level of anti-malaria protection induced by co-administration of pVAX-H-2K$^b$ and a sub-optimal dose of AdPyCS, the immunized mice are challenged with $1 \times 10^4$ of live *P. yoelii* sporozoites two, four and eight weeks later. AdPyCS-immunized mice receiving no pVAX-H-2K$^b$, as well as non-immunized mice, are used as controls. Forty-two hours after the challenge, the livers are removed from all the groups of mice and the levels of parasite rRNA are determined by a real-time quantitative RT-PCR.

Quantification of *P. yoelii* ribosomal RNA in the liver of sporozoite-challenged mice by real-time quantitative RT-PCR assay. A real-time quantitative PCR is adapted based on the 5'exonuclease activity of Taq polymerase (TaqMan assay) to quantify the parasite burden in the liver (Gonzles-Aseguinolaza et al., J. Exp. Med., 2002; 195:617-24) Briefly, total liver RNA is isolated by the method of Chomczynski and Sacchi (Chomczynski and Sacchi, Anal. Biochem., 162: 156-159, 1987) from mice sacrificed 42 h after intravenous injection with $1 \times 10^4$ *P. yoelii* sporozoites. After reverse transcription of the extracted RNA, cDNA is generated and its amount analyzed by real-time PCR, using the ABI Prism 5700 Sequence Detection system (PE Biosystems, Foster City, Calif.; Bruna-Romero et al., Int. J. Parasitol., 31: 1499-1502, 2001). Primers and fluorogenic probe with the following sequences is custom designed using the ABI Prism primer Express software (PE Biosystems, Foster City, Calif.), using *P. yoelii* (17XNL) 18S rRNA sequence (Bruna-Romero et al., Int. J. Parasitol., 31: 1499-1502, 2001). The primers, 5'-GGG-GATTGGTTTTGACGTTTTTGCG-3' (forward primer) (SEQ ID NO: 23), and 5'-AAGCATTAAATAAAGC-GAATACATCCTTAT-3' (reverse primer) (SEQ ID NO: 24) obtained from Operon Technologies Inc. (Alameda, Calif.). The specific fluorogenic probe, PyNYU, 5'-FAMCAATTG-GTTTACCTTTTGCTCTTT-TAMRA-3', (SEQ ID NO: 25) is obtained from PE Applied biosystems (Foster City, Calif.), and is generated with 5-propyne-2'-deoxyuridine (turbo Taqman probe) to achieve a proper Tm. The reaction mix contained 5 µl of 10× Taqman buffer A (PE Biosystems, Foster City, Calif.), 3.5 mM MgCl$_2$, 200 µM dNTP, 0.3 µM forward primer, 0.3 µM reverse primer, 50 nM turbo Taqman probe PyNYU, 1.25 U AmpliTaq Gold DNA polymerase, and water up to 50 µl final reaction volume. The temperature profile included 95° C. for 10 minutes and 35 cycles of denaturation at 95° C. for 15 seconds and annealing/extension at 60° C. for 1 minute. The PCR products are visualized in 2% agarose-1× TAE (50 mM Tris-acetate, pH 8.0, 1 mM EDTA) gels stained with 0.5 mg/ml ethidium bromide. Digital images from the gels are obtained using the Gel Doc 2000 gel documentation system (BioRad, Hercules, Calif.), and analyzed by densitometry using Quantity One software (BioRad, Hercules, Calif.). The precise amount of parasite-derived 18S cDNA molecules detected in this assay is determined by linear regression analysis using CT values obtained from both liver samples and those obtained from a standard curve generated with known amounts of plasmid 18S cDNA.

7.13. Example 6

Treating an Autoimmune Disease Using pVAX-H-2K$^b$ as an Adjuvant

7.13.1. Methods

Mice manipulations, plasmid construction, and route of administration are as described in Examples 1 and 3, supra.

Injection with OVA and challenge. To determine the adjuvant effects of allo/syngeneic MHC antigens on vaccines against autoimmune diseases, BALB/c mice are injected i.m. in the quadriceps muscles with 100 µg of plasmid DNA encoding ovalbumin (OVA) plasmid DNA in the presence of different amounts of pVAX-H-2K$^b$ ranging from 5 ng to 5 µg in a final volume of 100 µl 0.9% NaCl, divided bilaterally. On day 17, the mice are boosted i.m. with the same amount of plasmid DNA. The mice are then sensitized to OVA protein using an established protocol for the induction of airway hyperresponsiveness (AHR) in BALB/c mice (Maecker et al., J. Immunol. 2001: 166(2): 959-65). OVA (50 µg) adsorbed to 2 mg aluminum potassium sulfate (alum) is administered i.p. on days 24 and 38, followed by 50 µg OVA in 50 µl PBS given i.n. on days 38, 49, 50, and 51. Control mice received i.p. injections of alum alone and i.n. PBS. One day after the last i.n. challenge (day 52), AHR is measured in conscious mice after inhalation of increasing concentrations of methacholine (see below).

Measurement of airway responsiveness. Airway responsiveness is assessed by methacholine-induced airflow obstruction from conscious mice placed in a whole body plethysmograph (model PLY 3211; Buxco Electronics, Troy, N.Y.). Pulmonary airflow obstruction is measured by Penh using the following formula: Penh=((Te/RT−1)×(PEF/PIF), where Penh=enhanced pause (dimensionless), Te=expiratory time, RT=relaxation time, PEF=peak expiratory flow (ml/s), and PIF=peak inspiratory flow (ml/s). Enhanced pause (Penh), minute volume, tidal volume, and breathing frequency is obtained from chamber pressure, measured with a transducer (model TRD5100) connected to preamplifier modules (model MAX2270), and analyzed by system XA software (model SFT 1810). Measurements of methacholine responsiveness is obtained by exposing mice for 2 min to aerosolized 0.9% NaCl produced by a sonicator (Portable Ultrasonic, 5500D; DeVilbiss Health Care, Sommerset, Pa.), followed by incremental doses (2.5-20 mg/ml) of aerosolized methacholine. Results are expressed for each methacholine concentration as the percentage of baseline Penh values after 0.9% NaCl exposure.

\* \* \*

The present invention is not to be limited in scope by the specific embodiments described herein. Indeed, various modifications of the invention in addition to those described herein will become apparent to those skilled in the art from the foregoing description and the accompanying figures.

Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for augmenting an immune response to a malaria-specific antigen in a mammal comprising conjointly administering to the mammal: (i) the malaria-specific antigen in a first amount, and (ii) an a vector or a cell encoding allogenic MHC molecule in a second amount; the first and second amounts being effective in combination to augment the immune response mounted against the antigen by the mammal as compared to the immune response that the mammal could have mounted upon the administration of the first amount of the antigen without the conjoint administration of the vector or cell encoding the MHC molecule, wherein said MHC molecule induces an allo-reactive T cell response.

2. The method of claim 1, wherein augmenting the immune response is manifested by the enhancement or extension of the duration of antigen-specific CD4+ or CD8+T cell responses.

3. The method of claim 1, wherein the mammal is a mouse.

4. The method of claim 1, wherein the mammal is a human.

5. The method of claim 1, wherein the MHC molecule is an MHC class I molecule.

6. The method of claim 1, wherein the MHC molecule is an MHC class II molecule.

7. The method of claim 1, wherein the MHC molecule is selected from the group consisting of H2-K, H-2D, H2-L, H24A, H2-IE and.

8. The method of claim 1, wherein the MHC molecule is selected from the group consisting of HLA-A, HLA-B, HLA-C, HLA-DR, HLA-DP and HLA-DQ.

9. The method of claim 8, wherein the MHC molecule is selected from the group consisting of HLA-A*43, HLA-A*69, HLA-A*80, HLA-13*59, HLA-B*81, HLA-B*82, HLA-Cw* 14, HLA-Cw*18, HLA-DRB I*16, HLA-DQA 1*06, HLA-DPA 1*04, HLA-DPB 1 *33 and HLA-DPB 1*41.

10. The method of claim 1, wherein the antigen and the the vector or cell encoding MHC molecule are administered simultaneously to the mammal.

11. The method of claim 1, wherein the malaria-specific antigen is administered in the range of 0.01 mg -1 mg per kg of body weight.

12. The method of 1, wherein the antigen and the vector or cell encoding the MHC molecule are administered intramuscularly.

13. The method of claim 1, wherein the antigen and the vector or cell encoding the MHC molecule are administered intradermally.

14. The method of claim 1, wherein the antigen and the vector or cell encoding the MHC molecule are administered intranasally.

15. The method of claim 1, wherein the antigen and the vector or cell encoding the MHC molecule are administered subcutaneously.

16. The method of claim 1, wherein the antigen and the vector or cell encoding the MHC molecule are administered orally.

17. The method of claim 1, wherein the antigen and the vector or cell encoding the MHC molecule are administered to the mammal at the same site.

18. The method of claim 1, wherein the antigen is selected from the group consisting of protein, peptide, polysaccharide, glycoprotein, and glycolipid.

19. A method for augmenting an immune response to a sporozoite stage of malaria in a susceptible mammalian host comprising conjointly administering to the host: (i) at least one malaria sporozoite-specific antigen in a first amount, and (ii) a vector or a cell encoding an allogenic MHC molecule in a second amount; the first and second amounts being effective in combination to augment the immune response mounted against the antigen by the host as compared to the immune response that the host could have mounted upon the administration of the first amount of the antigen without the conjoint administration of the vector or cell encoding the MHC molecule, wherein said MHC molecule induces an allo-reactive T cell response.

20. The method of claim 19, wherein the sporozoite-specific antigen comprises at least one T-cell and/or B-cell epitope of a plasmodial protein or a fragment thereof.

21. The method of claim 20, wherein the plasmodial protein is derived from a plasmodium selected from the group consisting of *P. falciparum, P. vivax, P. malariae, P. ovale, P. reichenowi, P. knowlesi, P. cynomolgi, P. brasilianum, P. yoelii, P. berghei*, and *P. chabaudi*.

22. The method of claim 20, wherein the plasmodial protein is circumsporozoite (CS) protein.

23. The method of claim 19, wherein the sporozoite-specific antigen comprises the *P. yoelii* CS protein (AdPyCS).

24. The method of claim 19, wherein the sporozoite-specific antigens comprises irradiated plasmodial sporozoites.

25. The method of claim 19, wherein augmenting the immune response is manifested by the enhancement or extension of the duration of antigen-specific CD4+or CD8+T cell responses.

* * * * *

UNITED STATES PATENT AND TRADEMARK OFFICE
CERTIFICATE OF CORRECTION

| | |
|---|---|
| PATENT NO. | : 9,155,789 B2 |
| APPLICATION NO. | : 11/412149 |
| DATED | : October 13, 2015 |
| INVENTOR(S) | : Moriya Tsuji |

It is certified that error appears in the above-identified patent and that said Letters Patent is hereby corrected as shown below:

In the Claims:

At column 51, claim number 1, line number 36, please replace "in a first amount, and (ii) an a vector or a cell encoding" with --in a first amount, and (ii) a vector or a cell encoding an-- therefor.

At column 51, claim number 7, line number 58, please replace "H24A, H2-IE and" with --H24A, and H2-IE-- therefor.

At column 52, claim number 10, line number 32, please replace "The method of claim 1, wherein the antigen and the the vector or cell encoding MHC molecule" with --The method of claim 1, wherein the antigen and the vector or cell encoding the MHC molecule-- therefor.

At column 52, claim number 19, line number 63, please replace "(ii) a vector or a cell encoding an allogenic MHC molecule in" with --(ii) a vector or cell encoding an allogenic MHC molecule in-- therefor.

Signed and Sealed this
Twenty-third Day of August, 2016

Michelle K. Lee
*Director of the United States Patent and Trademark Office*